US 11,478,755 B2

(12) United States Patent
Wegener et al.

(10) Patent No.: US 11,478,755 B2
(45) Date of Patent: Oct. 25, 2022

(54) SMALL VOLUME PROCESSING SYSTEMS AND METHODS

(71) Applicant: Fenwal, Inc., Lake Zurich, IL (US)

(72) Inventors: Christopher J. Wegener, Libertyville, IL (US); Bret M. Olson, Chicago, IL (US); Carolyn Kos, Chicago, IL (US); Timothy Getschman, Racine, WI (US); Mark J. Brierton, Cary, IL (US); Robert A. Brown, Algonquin, IL (US)

(73) Assignee: Fenwal, Inc., Lake Zurich, IL (US)

( * ) Notice: Subject to any disclaimer, the term of this patent is extended or adjusted under 35 U.S.C. 154(b) by 428 days.

(21) Appl. No.: 16/541,559

(22) Filed: Aug. 15, 2019

(65) Prior Publication Data

US 2021/0046426 A1   Feb. 18, 2021

(51) Int. Cl.
*B01D 63/16* (2006.01)
*A01N 1/02* (2006.01)

(52) U.S. Cl.
CPC .......... *B01D 63/16* (2013.01); *A01N 1/0242* (2013.01); *B01D 2313/10* (2013.01); *B01D 2313/243* (2013.01); *B01D 2313/50* (2013.01)

(58) Field of Classification Search
CPC ................ A01N 1/0242; A61M 1/265; A61M 2205/128; B01D 2313/10; B01D 2313/243; B01D 2313/50; B01D 63/16
See application file for complete search history.

(56) References Cited

U.S. PATENT DOCUMENTS

| 5,053,121 | A | 10/1991 | Schoendorfer et al. |
| 5,194,145 | A | 3/1993 | Schoendorfer |
| 5,789,147 | A | 8/1998 | Rubinstein et al. |
| 5,840,502 | A | 11/1998 | Van Vlasselaer |
| 5,868,696 | A | 2/1999 | Giesler et al. |
| 6,325,775 | B1 | 12/2001 | Thom et al. |
| 6,464,624 | B2 | 10/2002 | Pages |

(Continued)

FOREIGN PATENT DOCUMENTS

| EP | 1254675 | 11/2002 |
| EP | 1674120 B1 | 8/2009 |

(Continued)

OTHER PUBLICATIONS

Extended European Search Report, counterpart European App. No. 20190973.6 (dated Jan. 25, 2021) (7 pages).

*Primary Examiner* — Dirk R Bass
(74) *Attorney, Agent, or Firm* — Cook Alex Ltd.

(57) ABSTRACT

A fluid processing system includes a disposable fluid circuit and reusable hardware configured to accept the disposable fluid circuit. The disposable fluid circuit includes a spinning membrane separator, first and second syringes, and a flow control cassette. The reusable hardware includes a spinning membrane separator drive coupled to the spinning membrane separator, first and second syringe pumps coupled to the first and second syringes respectively, a control cassette interface coupled to the flow control cassette, and at least one controller coupled to the spinning membrane separator drive, the first and second syringe pumps, and the control cassette interface. The controller is configured to selectively operate the drive, the first and second syringe pumps, and the interface to provide a procedure according to a protocol.

20 Claims, 12 Drawing Sheets

(56) References Cited

U.S. PATENT DOCUMENTS

| | | |
|---|---|---|
| 6,471,855 B1 | 10/2002 | Odak et al. |
| 6,582,386 B2 | 6/2003 | Min et al. |
| 6,706,008 B2 | 3/2004 | Vishnoi et al. |
| 6,709,378 B2 | 3/2004 | Nishimura et al. |
| 6,716,151 B2 | 4/2004 | Panzani et al. |
| 6,733,433 B1 | 5/2004 | Fell |
| 6,808,503 B2 | 10/2004 | Farrell et al. |
| 6,884,228 B2 | 4/2005 | Brown et al. |
| 7,011,852 B2 | 3/2006 | Sukavaneshvar et al. |
| 7,179,391 B2 | 2/2007 | Leach et al. |
| 7,232,430 B2 | 6/2007 | Carlisle et al. |
| 7,238,164 B2 | 7/2007 | Childers et al. |
| 7,291,450 B2 | 11/2007 | Sowemimo-Coker et al. |
| 7,364,657 B2 | 4/2008 | Mandrusov et al. |
| 7,374,678 B2 | 5/2008 | Leach et al. |
| 7,465,285 B2 | 12/2008 | Hutchinson et al. |
| 7,476,209 B2 | 1/2009 | Gara et al. |
| 7,648,627 B2 | 1/2010 | Beden et al. |
| 7,744,554 B2 | 6/2010 | Howard |
| 7,867,189 B2 | 1/2011 | Childers et al. |
| 7,909,795 B2 | 3/2011 | Childers et al. |
| 8,075,546 B2 | 12/2011 | Carlisle et al. |
| 8,096,186 B2 | 1/2012 | Butterfield |
| 8,101,077 B2 | 1/2012 | Sukavaneshvar et al. |
| 8,114,276 B2 | 2/2012 | Childers et al. |
| 8,142,653 B2 | 3/2012 | Beden et al. |
| 8,206,338 B2 | 6/2012 | Childers et al. |
| 8,323,492 B2 | 12/2012 | Childers et al. |
| 8,328,758 B2 | 12/2012 | Childers et al. |
| 8,329,030 B2 | 12/2012 | Childers et al. |
| 8,377,293 B2 | 2/2013 | Beden et al. |
| 8,435,408 B2 | 5/2013 | Beden et al. |
| 8,439,889 B2 | 5/2013 | Sano |
| 8,679,054 B2 | 3/2014 | Childers et al. |
| 8,721,883 B2 | 5/2014 | Lauer |
| 8,740,836 B2 | 6/2014 | Childers et al. |
| 8,740,837 B2 | 6/2014 | Childers et al. |
| 8,808,551 B2 | 8/2014 | Leach et al. |
| 8,834,719 B2 | 9/2014 | Childers et al. |
| 8,926,835 B2 | 1/2015 | Beden et al. |
| 8,932,469 B2 | 1/2015 | Childers et al. |
| 8,961,787 B2 | 2/2015 | Wood et al. |
| 8,986,185 B2 | 3/2015 | Del Vecchio |
| 9,101,709 B2 | 8/2015 | Beden et al. |
| 9,119,914 B2 | 9/2015 | Nguyen et al. |
| 9,283,312 B2 | 3/2016 | Childers et al. |
| 9,352,021 B2 | 5/2016 | Hanna et al. |
| 9,452,254 B2 | 9/2016 | Kimura et al. |
| 9,459,186 B2 | 10/2016 | Mastromatteo et al. |
| 9,603,986 B2 | 3/2017 | Kusters et al. |
| 9,717,842 B2 | 8/2017 | Min et al. |
| 9,744,498 B2 | 8/2017 | Wegener |
| 9,795,729 B2 | 10/2017 | Childers et al. |
| 9,827,359 B2 | 11/2017 | Beden et al. |
| 9,855,377 B2 | 1/2018 | Childers et al. |
| 9,907,899 B2 | 3/2018 | Kim |
| 9,925,320 B2 | 3/2018 | Childers et al. |
| 10,329,530 B2 | 6/2019 | Wegener |
| 10,413,652 B2 | 9/2019 | Foley et al. |
| 10,471,194 B2 | 11/2019 | Beden et al. |
| 10,525,184 B2 | 1/2020 | Childers et al. |
| 10,578,092 B2 | 3/2020 | Overson et al. |
| 10,695,479 B2 | 6/2020 | Childers et al. |
| 10,912,875 B2 | 2/2021 | Beiriger |
| 10,941,760 B2 | 3/2021 | Overson et al. |
| 2002/0004015 A1 | 1/2002 | Carlisle et al. |
| 2005/0049539 A1 | 3/2005 | O'Hara, Jr. et al. |
| 2006/0002824 A1* | 1/2006 | Chang ............... B01L 3/0293 422/400 |
| 2006/0217651 A1 | 9/2006 | Hutchinson et al. |
| 2006/0219644 A1 | 10/2006 | O'Hara, Jr. et al. |
| 2006/0224099 A1 | 10/2006 | Hutchinson et al. |
| 2008/0103429 A1 | 5/2008 | Shang et al. |
| 2008/0171951 A1 | 7/2008 | Fell |
| 2009/0107902 A1* | 4/2009 | Childers ............... B01D 61/30 210/196 |
| 2011/0124106 A1 | 5/2011 | Froman et al. |
| 2011/0218487 A1 | 9/2011 | Shang et al. |
| 2012/0181225 A1 | 7/2012 | Weis |
| 2013/0092630 A1 | 4/2013 | Wegener |
| 2013/0341291 A1 | 12/2013 | Wegener et al. |
| 2014/0074062 A1* | 3/2014 | Caffey ............... A61M 5/1452 604/82 |
| 2014/0199680 A1 | 7/2014 | Min et al. |
| 2015/0080204 A1 | 3/2015 | Kassis |
| 2015/0101707 A1 | 4/2015 | Ranalletta et al. |
| 2016/0252434 A1 | 9/2016 | Smith et al. |
| 2017/0204371 A1 | 7/2017 | Wegener |
| 2018/0015418 A1 | 1/2018 | Binninger et al. |
| 2018/0155070 A1 | 6/2018 | Min et al. |
| 2019/0231949 A1 | 8/2019 | Igarashi |
| 2019/0290830 A1 | 9/2019 | Igarashi |
| 2019/0351113 A1 | 11/2019 | Min et al. |
| 2019/0351126 A1 | 11/2019 | Foley et al. |
| 2020/0121842 A1 | 4/2020 | Childers et al. |
| 2020/0297909 A1 | 9/2020 | Suljevic et al. |
| 2020/0324035 A1 | 10/2020 | Childers et al. |
| 2021/0046426 A1 | 2/2021 | Wegener et al. |

FOREIGN PATENT DOCUMENTS

| | | |
|---|---|---|
| EP | 1512418 B1 | 10/2009 |
| EP | 2298376 A1 | 3/2011 |
| EP | 1585565 B1 | 7/2011 |
| EP | 1251922 | 8/2011 |
| EP | 1372778 B1 | 6/2012 |
| EP | 1126885 B1 | 7/2012 |
| EP | 2308526 B1 | 3/2013 |
| EP | 1365831 B1 | 4/2013 |
| EP | 1425054 B1 | 12/2013 |
| EP | 1509260 B1 | 4/2014 |
| EP | 2224975 B1 | 7/2014 |
| EP | 2295090 B1 | 1/2015 |
| EP | 2308525 B1 | 3/2015 |
| EP | 2535070 B1 | 12/2015 |
| EP | 2695625 B1 | 12/2015 |
| EP | 2167163 B1 | 2/2016 |
| EP | 2298378 B1 | 3/2016 |
| EP | 2550518 B1 | 4/2016 |
| EP | 2295091 B1 | 4/2017 |
| EP | 3192541 | 7/2017 |
| EP | 3009155 B1 | 10/2017 |
| EP | 3257532 A1 | 12/2017 |
| EP | 2696961 B1 | 2/2019 |
| EP | 3569266 A1 | 11/2019 |
| EP | 3782670 A1 | 2/2021 |
| WO | WO01/17584 | 3/2001 |
| WO | WO02/04046 | 1/2002 |
| WO | WO02/04048 | 1/2002 |
| WO | WO02/056992 | 7/2002 |
| WO | WO02/070033 | 9/2002 |
| WO | WO02/070034 | 9/2002 |
| WO | WO02/070035 | 9/2002 |
| WO | WO02/070062 | 9/2002 |
| WO | WO03/101510 | 12/2003 |
| WO | WO2004/060449 | 7/2004 |
| WO | WO2009/006501 | 1/2009 |
| WO | WO2009/055639 | 4/2009 |
| WO | WO2011/119348 | 9/2011 |
| WO | WO 2012/125470 | 9/2012 |
| WO | WO2012/141697 | 10/2012 |
| WO | WO2016/057364 | 4/2016 |
| WO | WO2017/161319 | 9/2017 |
| WO | WO2018/051982 | 3/2018 |
| WO | WO 2018/065880 | 4/2018 |
| WO | WO2019/188501 | 10/2019 |
| WO | WO2020/191156 | 9/2020 |
| WO | WO2020/208532 | 10/2020 |

* cited by examiner

SMALL VOLUME PROCESSING SYSTEMS AND METHODS

TECHNICAL FIELD

The present disclosure is generally directed to systems and methods for processing (e.g., washing) suspensions of cells. More particularly, the present disclosure is directed to systems and methods for processing small volumes of cells using a disposable fluid circuit and a reusable processing machine or hardware to generate a cell product.

BACKGROUND

A number of well-known therapies are currently practiced in which a targeted cellular blood component (e.g., red blood cells, white blood cells, and platelets) is separated from whole blood and stored for later infusion to a patient. The targeted cell product (e.g., red blood cells, white blood cells, or platelets) may be in a suspension that includes plasma and/or some other supernatant. As such, it is sometimes desirable to "wash" the cellular suspension (typically with a physiologic buffer) to remove the plasma/supernatant, as well as any non-target cellular material, prior to reinfusion.

Systems and methods for cell washing are exemplified by US Pub. Nos. 2013/0341291, 2013/0092630, and 2014/0199680, each of which is incorporated herein by reference. Each of these published applications discloses cell washing methods utilizing disposable fluid circuits including a spinning membrane separator and a reusable processing machine. Such machines include peristaltic pumps and pinch valves that act on the tubing of the fluid circuit to direct flow within the fluid circuit.

The fluid circuits in the published applications listed above have a relatively large internal volume, and thus require relatively large volumes of wash or flush media to clear processed fluid through the fluid circuit. While such systems and fluid circuits are capable of washing and reducing the volume of the targeted cell component into final volumes of ranging from approximately 50 mL to 5,000 mL, there are instances in which smaller final volumes (e.g., 10 mL) are desired, such as when processing single-dose quantities of mononuclear cell products. Thus, it would be desirable to provide systems and methods for processing (e.g., concentrating or washing) small volumes of cellular suspensions.

SUMMARY

In a first aspect, a fluid processing system includes a disposable fluid circuit and reusable hardware configured to accept the disposable fluid circuit. The disposable fluid circuit includes a spinning membrane separator having an inlet, a retentate outlet, and a filtrate outlet, first and second syringes, and a flow control cassette including a housing containing a plurality of separate channels connected at a plurality of selectable junctions, each of the selectable junctions selectively connecting at least two of the plurality of channels, the channels and selectable junctions defining at least a first path between a source container, the spinning membrane inlet, the filtrate outlet and the first syringe, a second path between the first syringe and a filtrate container, and a third path between a wash media container, the spinning membrane inlet, the retentate outlet and the second syringe. The reusable hardware includes a spinning membrane separator drive coupled to the spinning membrane separator, first and second syringe pumps, the first and second syringes coupled to the first and second syringe pumps respectively, the first syringe pump configured to move a piston within the first syringe and the second syringe pump configured to move a piston within the second syringe, a control cassette interface having at least one actuator for each of the selectable junctions, and at least one controller coupled to the spinning membrane separator drive, the first and second syringe pumps, and the control cassette interface, the controller configured to selectively operate the drive, the first and second syringe pumps, and the interface to provide a procedure according to a protocol.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
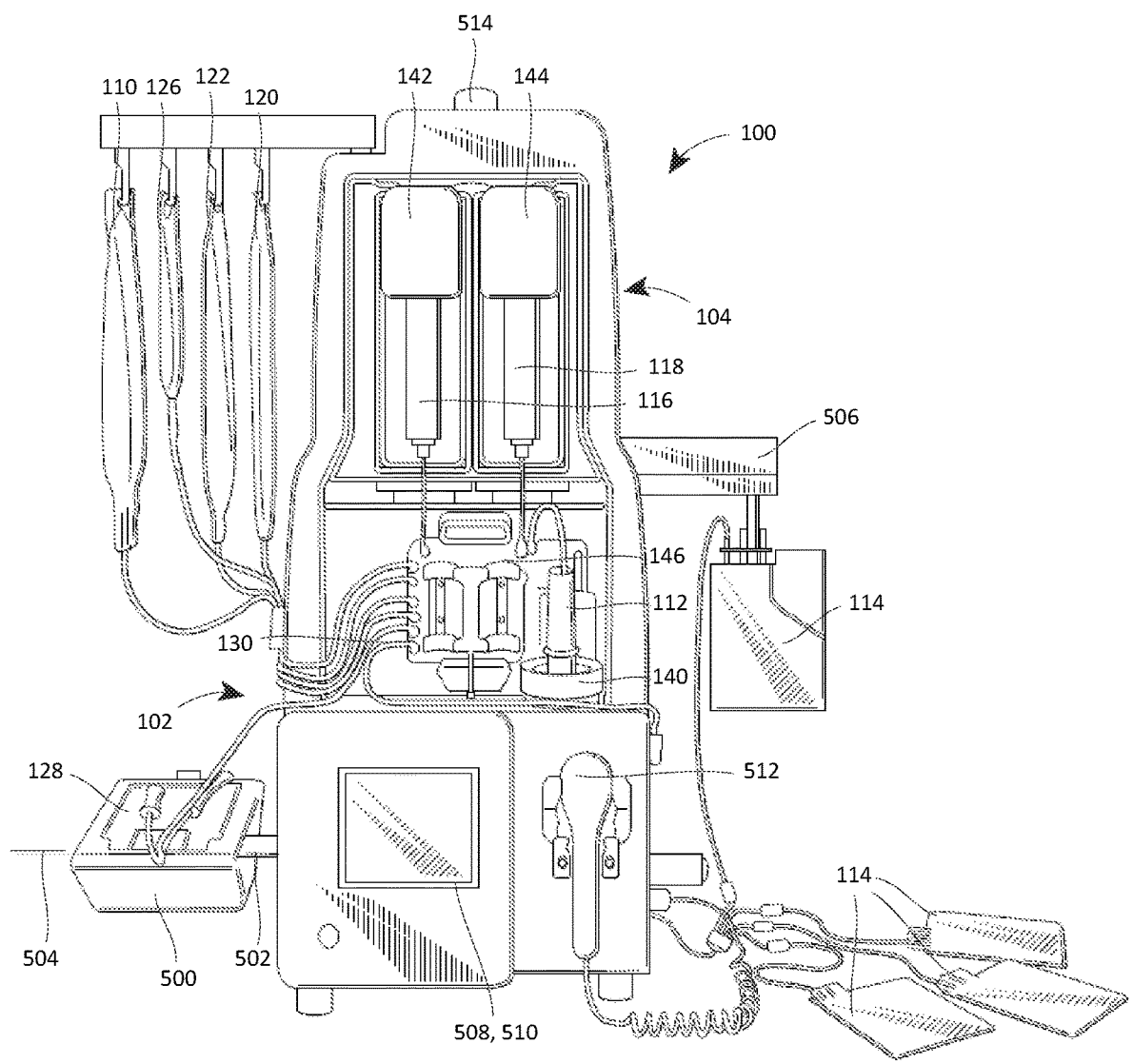
FIG. 1 is a perspective view of a system for processing (e.g., concentrating or washing) small volumes of cellular suspensions including a disposable fluid circuit and a reusable processing machine or hardware.

Turning first to FIG. 1, an embodiment of a system 100 for processing fluids, such as cell suspensions (e.g., cell washing), is illustrated, the system 100 including a disposable fluid circuit (also referred to as a set or kit) 102 and a reusable processing machine, or hardware, 104.

Figure 2:
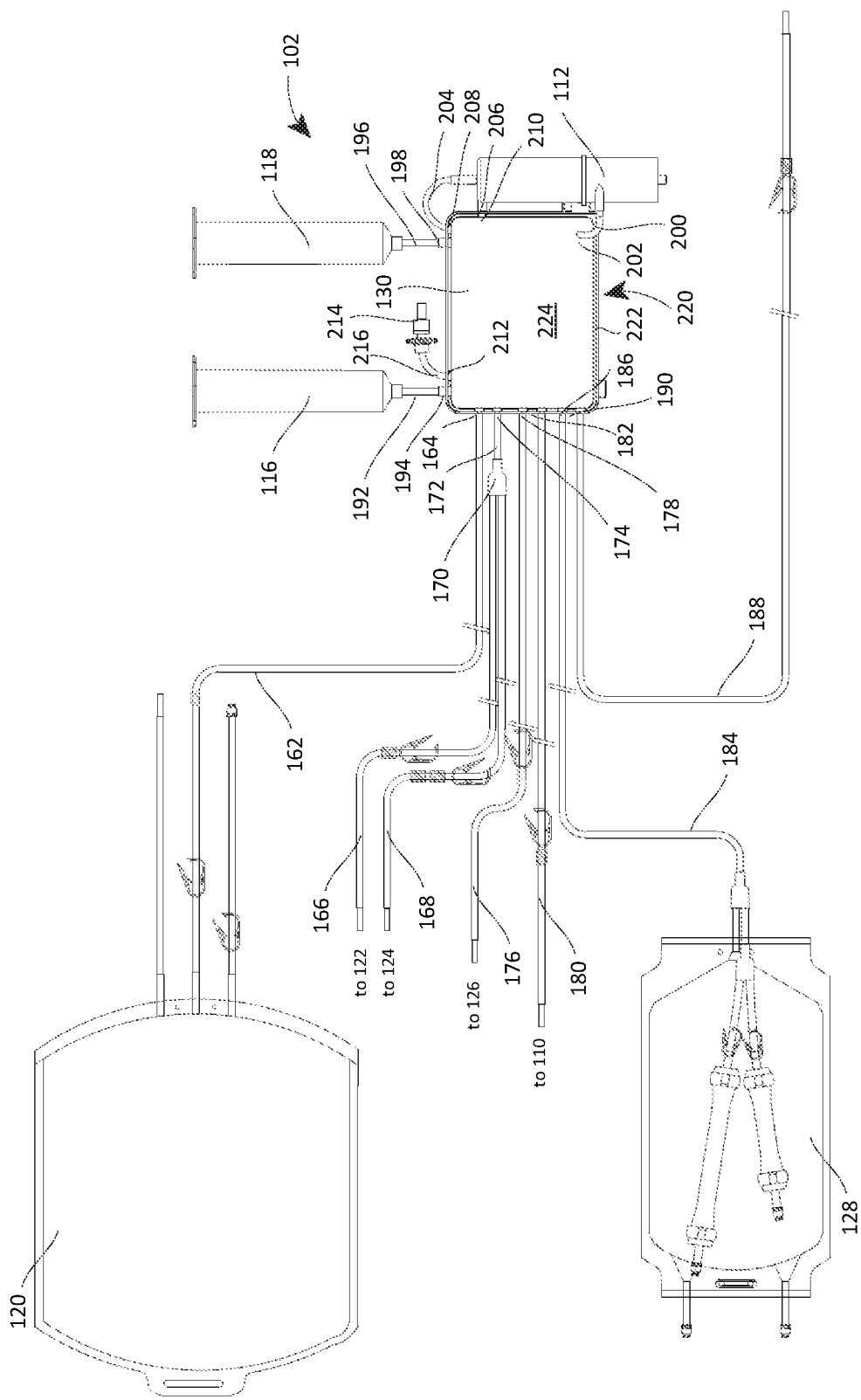
FIG. 2 is a plan view of an embodiment of a disposable fluid circuit for use in the system of FIG. 1.

As seen in FIGS. 1 and 2, the disposable fluid circuit 102 is connectable to a source container 110 of fluid, in particular biological fluid. The disposable fluid circuit 102 includes a spinning membrane separator 112 that is used to process the fluid received from the source container 110, and to direct a portion of that fluid into one of more product containers 114. These containers may be in the form of flexible bags according to the illustrated embodiment. The flow of fluid from the source container 110, through the spinning membrane separator 112, and to the one or more product containers 114 is achieved through the use of first and second syringes 116, 118, which are in fluid communication with the source container 110, the spinning membrane separator (or spinning membrane for short) 112, and the one or more product containers 114. The syringes 116, 118 also may be in fluid communication with a number of other containers 120, 122, 124, 126, 128 (container 124 being schematically represented in FIG. 2 only).

The flow of the fluid between the containers 110, 114, 120, 122, 124, 126, 128, the spinning membrane 112, and the syringes 116, 118 is controlled using a flow control cassette 130, which cassette 130 may be connected to each of the foregoing by tubing, or lines. In addition, the cassette 130 may include internal flow paths that are defined in part by a plurality of separate channels or passages, which in turn may be contained within and may be defined by the structure (e.g., housing) of the cassette 130. The channels may be connected at a plurality of selectable junctions, which may control the flow of fluid from one channel to another. These selectable junctions may also be referred to as valves, valve stations, or clamps, because, as illustrated, the selectable junctions provide controlled access between the channels. The cassette 130 may also include sensor stations, by which sensors may be associated with the flow paths within the cassette 130 to determine characteristics of the flow therein, such as pressure, presence of air and/or fluid, or optical properties. Preferably, the length of each of the lines and channels is kept as short as possible to further minimize the internal volume of the fluid circuit 102.

As illustrated in FIG. 2, the spinning membrane 112 and the syringes 116, 118 may be integrally formed as part of (i.e., as one piece with) the cassette 130, so as to further reduce the tubing volume associated with the kit 14. According to other embodiments, the spinning membrane 112 and/or the syringes 116, 118 may be attached to the remainder of the fluid circuit 102 at the time of use, as may be the case with one or more of the containers 110, 114, 120, 122, 124, 126, 128. Again, as illustrated in FIG. 2, the container 120 and container 128 are integrally formed with the cassette 130.

Figure 3:
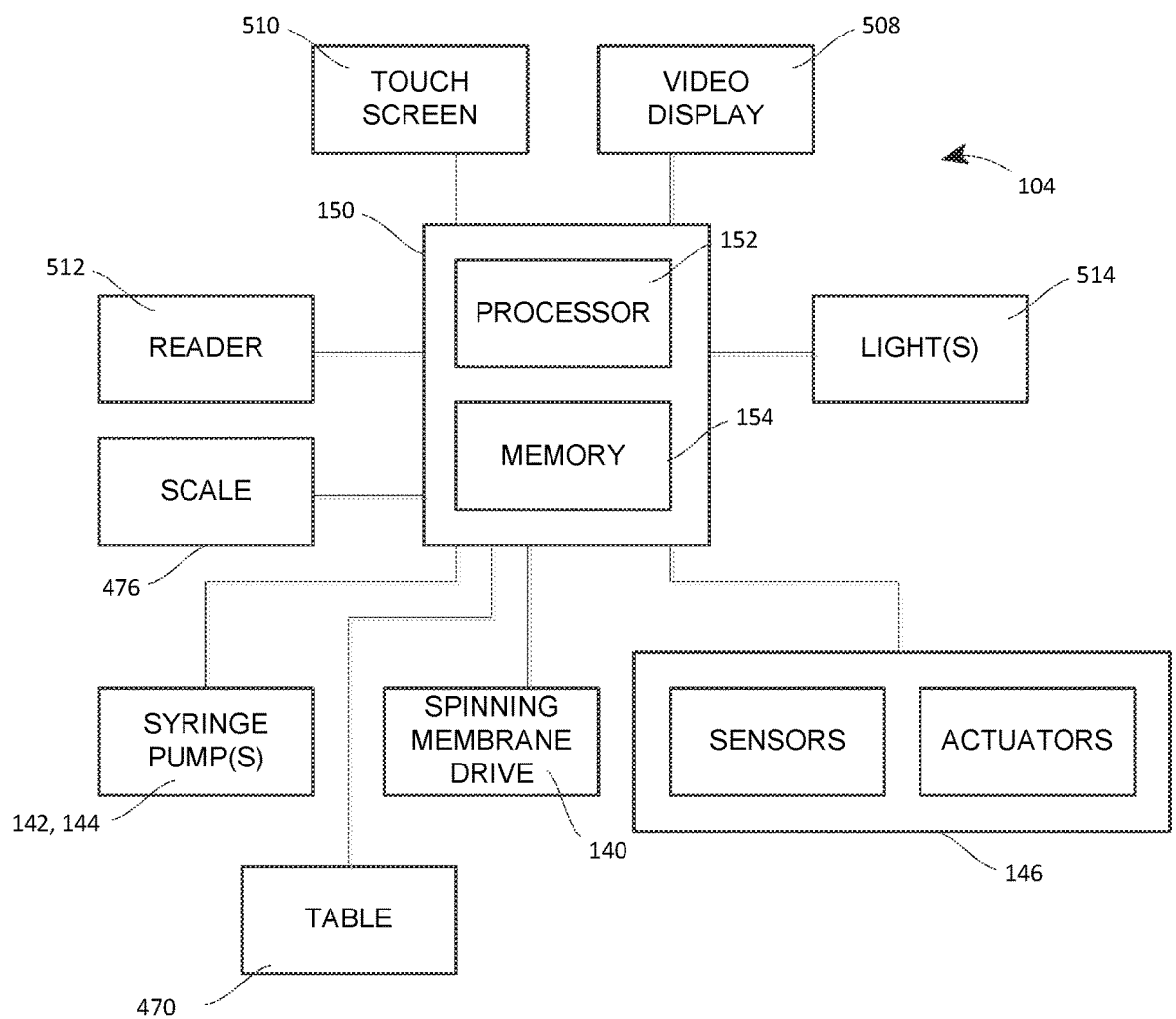
FIG. 3 is a block diagram of an embodiment of the reusable processing machine or hardware of FIG. 1.

As seen in FIGS. 1 and 3, the reusable hardware component (or reusable hardware for short) 104 includes a drive 140 for the spinning membrane separator 112, a syringe pump 142, 144 for each syringe 116, 118, and a control cassette interface 146 that is associated with the flow control cassette 130 when the fluid circuit 102 is disposed on the hardware 104 (e.g., is mounted on the hardware 104). As will be explained in detail below, the cassette interface 146 includes actuators and sensors that are associated with the clamps and sensor stations of the flow control cassette 130, and are configured to operate the clamps or sense characteristics of the fluid, respectively.

The reusable hardware 104 also includes a controller 150 that is configured to control operation of the system 100, for example using a method of operation as is explained below relative to FIGS. 13 and 14. The controller 150 may include a microprocessor 152 (which, in fact may include multiple physical and/or virtual processors). According to other embodiments, the controller 150 may include one or more electrical circuits designed to carry out the actions described herein. In fact, the controller 150 may include a microprocessor 152 and other circuits or circuitry. In addition, the controller 150 may include one or more memories 154. The instructions by which the microprocessor 150 is programmed may be stored on the one or more memories 154 associated with the microprocessor 150, which memory/memories 154 may include one or more tangible non-transitory computer readable memories, having computer executable instructions stored thereon, which when executed by the microprocessor 152, may cause the microprocessor 152 to carry out one or more actions as described below.

The controller 150 may be coupled (i.e., directly or indirectly connected) to the equipment of the reusable hardware 104, such as the spinning membrane drive 140, the first syringe pump 142, the second syringe pump 144, and the cassette interface 146. The controller 150 may operate each of these devices, each of which may be an assembly of other devices or equipment, to cause the fluid to flow through the fluid circuit 102 associated with the hardware 104, for example to cause fluid to flow from the source container 110, through the spinning membrane 112, and eventually into the product container(s) 114. For example, the controller 150 may be programmed to perform a process or procedure according to a protocol, such as to wash particular cells contained in the fluid within the source container 110, before they are distributed into one or more of the product containers 114. The controller 150 may be programmed to perform other actions as well, such as to test the fluid circuit 102, to prime the fluid circuit 102, to rinse parts of the circuit 102 after the wash has been performed, to add other components to the cell-containing fluid before that fluid is distributed to the product containers 114, and to distribute the cell-containing fluid into the product containers 114.

Having thus described the structure and operation of the system 100, including the fluid circuit 102 and reusable hardware 104, in general terms, the details of each of the systems is now discussed, starting with the fluid circuit 102.

As mentioned above, the flow of fluids through the fluid circuit 102 is controlled through the flow control cassette 130. While other embodiments may involve fluid circuits 102 where some of the fluid does not pass through the cassette 130, according to the illustrated embodiment, the fluid flows between the containers 110, 114, 120, 122, 124, 126, 128, the spinning membrane 112, and the syringes 116, 118 via the cassette 130. As mentioned above, each of the containers 110, 114, 120, 122, 124, 126, 128, the spinning membrane 112, and the syringes 116, 118 is connected to the cassette through the use of medical grade tubing, or lines.

With reference to FIGS. 1 and 2, the container 120 used to receive the filtrate of the spinning membrane 112 and other fluids is connected via a line 162 to a filtrate container port 164 formed on the cassette 130. The first and second containers 122, 124, used to contain wash media as may be used during the method of operation of the system 100, each may be connected to a line 166, 168 that are connected at a first end to the containers 122, 124, and at a second end to a Y-junction 170. The Y-junction 170 is, in turn, connected via a line 172 to a wash container port 174. The container 126, which may contain a cryopreservation agent (CPA) according to one embodiment, is connected via a line 176 to a port 178. The source container 110 may be connected via a line 180 to a source container port 182. Further, a secondary container 128 is connected via a line 184 to a port 186, and the product container(s) 114 is/are connected via a line 188 to a product container port 190.

As is reflected in the illustrated embodiment, certain of the containers may be formed integrally with the fluid circuit 102, while other containers may be attached at the time of operation. For example, filtrate container 120 and the secondary container 128 are formed integrally with their respective lines 162, 188. On the other hand, lines 166, 168, 176, 180, 188 may be formed with an attachment site (such as an end formed to be sealed to the container or with a connector, such as a luer lock connector, attached thereto) to connect to the containers 110, 122, 124, 126, 114 at the time of use.

The syringe 116 may be connected via a line 192 to a port 194, and the syringe 118 may be connected via a line 196 to a port 198. In a similar fashion, the spinning membrane 112 may be connected at an inlet of the spinning membrane 112 by a line 200 to an inlet port 202, and at a first outlet via a line 204 to a first outlet port 208 and at a second outlet via a line 206 to a second outlet port 210. In addition, an air vent port 212 is provided, and the air vent port 212 is connected to a filter 214 via a line 216. Because of the proximity of the spinning membrane 112, the syringes 116, 118, and the filter 214 to the cassette 130, one or more of the lines 192, 196, 200, 204, 208, 216 may be defined by portions of cassette 130 itself.

Figure 7:
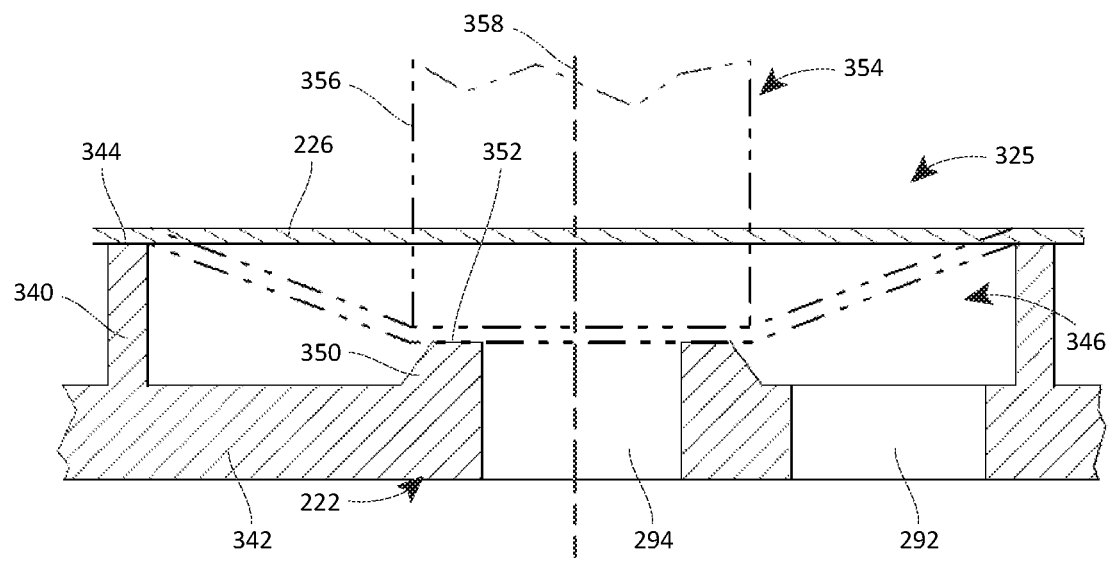
FIG. 7 is a cross-sectional view of one of the clamps of the flow control cassette being manipulated by an actuator.

According to the illustrated embodiment, and as seen in FIGS. 2 and 4-6, the cassette 130 includes a housing 220 defined by a frame 222 to which side walls 224, 226 are attached (see FIGS. 2 and 7). The walls 224, 226 may be attached about the periphery of the frame 222, as well as along structures of the frame that define the channels, clamps, and sensor stations discussed above. The walls 224, 226 may be attached through the use of joining techniques, such as ultrasonic welding, or may be attached by holding the wall 224, 226 and the frame 22 in contact with each other through the application of force.

A negative pressure may be drawn on the side wall 224 of the cassette 130. Drawing a negative pressure on the wall 224 of the cassette 130 is believed to prevent the collapse of the channels defined within the housing 220. This is particularly important in a system that uses syringes 116, 118 and syringe pumps 142, 144 in that the syringe pumps operate, at least in part, by drawing negative pressures within the fluid paths defined, at least in part, by the channels. The application of negative pressure to the wall 224 of the cassette 130 compensates, at least in part, for the negative pressures drawn within the fluid paths.

Figure 4:
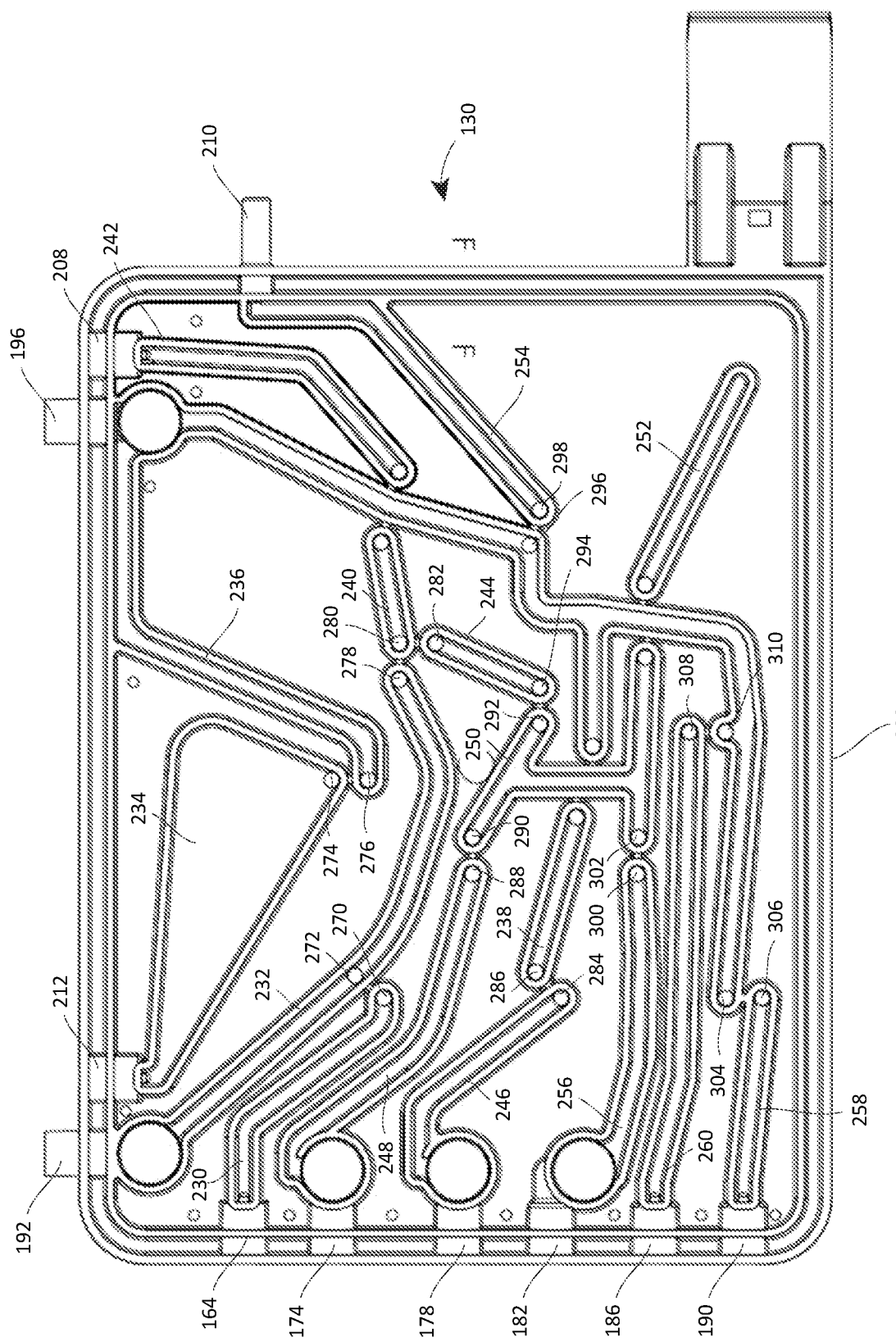
FIG. 4 is a side view of an embodiment of a flow control cassette for use in the disposable fluid circuit of FIG. 2, with one of the sidewalls removed for ease of illustration.

Turning next to FIG. 4, it will be noted that the frame 222 defines the afore-mentioned plurality of separate and distinct channels, which channels may be connected to one of the ports discussed above. The channels may also have one or more apertures disposed at locations along the lengths of the channel. These apertures may be used to connect the channels, via the clamps or sensor stations, for example, to other channels. Together, the channels may define flow paths (or fluid paths, or fluid flow paths) between the containers 110, 114, 122, 124, 126, 128, syringes 116, 118, and the spinning membrane 112.

Starting at the left-hand side of the cassette 130, a channel 230 is connected to the port 164, and includes an aperture 270. A channel 232 is connected to port 192, and includes apertures 272, 278. A channel 234 is connected to port 212, and includes aperture 274. A channel 236 is connected to port 196, and includes apertures 276, 296, 304, 310. A channel 238 includes an aperture 286, while a channel 240 includes an aperture 280. A channel 242 is connected to port 208, and is connected to channel 240 via a station and unnumbered apertures of channels 240, 242; in a similar fashion, channel 238 is connected to channel 236 via a station and unnumbered apertures of channels 236, 238.

Towards the middle of the cassette 130, a channel 244 includes apertures 282, 294. A channel 246 is attached to port 178, and includes aperture 284. A channel 248 is attached to port 174, and includes aperture 288. A channel 250 includes apertures 290, 292, 302. A channel 252 is connected to the inlet port 202 of the spinning membrane 112, and is connected to the channel 250 via a station and unnumbered apertures of channels 250, 252.

At the right-hand side of the cassette 130, a channel 254 is connected to port 210, and includes aperture 298. On the other hand, at the right-hand side of the page, a channel 256 is connected to port 182 and includes an aperture 300. A channel 258 is connected to port 190, and includes an aperture 306. Finally, a channel 260 is connected to port 186, and includes an aperture 308.

Figure 5:
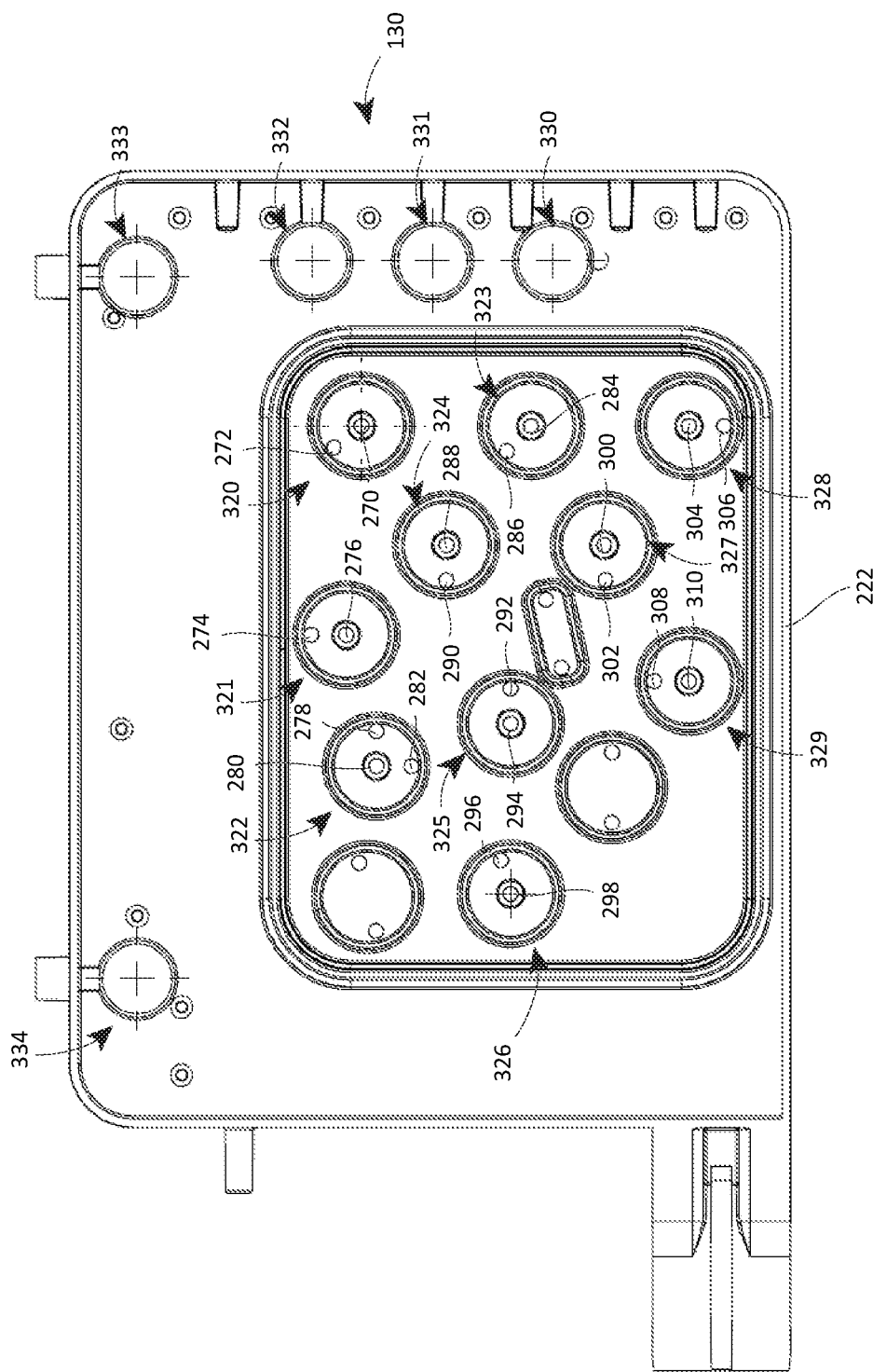
FIG. 5 is a side view of the embodiment of the flow control cassette of FIG. 4, illustrating the opposite side of the flow control cassette.
Figure 6:
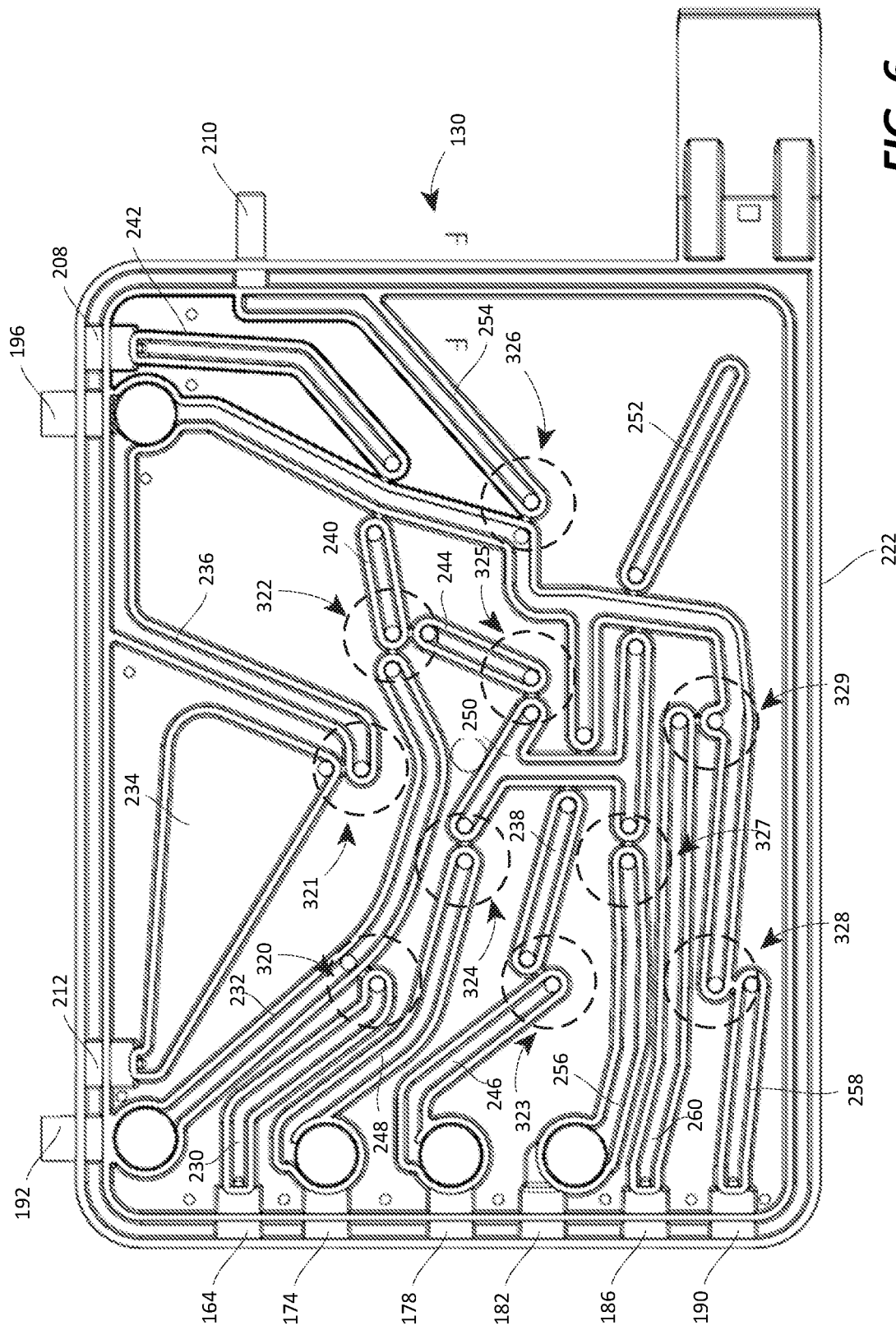
FIG. 6 is a side view of the embodiment of the flow control cassette of FIG. 4, with the location of the selectable junctions, or clamps, from the opposite side of the cassette illustrated relative to the channels and apertures illustrated in FIG. 4.

As seen in FIG. 5, each of the apertures included in the channels 236-260 is associated with one or more of the other apertures. In most instances, each aperture is associated with one of the other apertures; in one instance, three apertures are associated with each other. Each grouping of two or more apertures is associated with a chamber on the reverse side of the cassette 130 from that illustrated in FIG. 4, which chamber then defines one of the clamps.

In particular, apertures 270, 272 are grouped, and define in part a selectable junction or clamp 320, while apertures 274, 276 are grouped, and define in part a clamp 321. The apertures 278, 280, 282 are grouped, and define in part a clamp 322. The apertures 284, 286 define in part a clamp 323, the apertures 288, 290 define in part a clamp 324, the apertures 292, 294 define in part a clamp 325, and the apertures 296, 298 define in part a clamp 326. Finally, the apertures 300, 302 define in part a clamp 327, the apertures 304, 306 define in part a clamp 328, and the apertures 308, 310 define in part a clamp 329. The clamps 320-329 are also shown in dashed line in FIG. 6 with the markings of the apertures removed, for ease of illustration relative to the associations of the clamps 320-329 with the channels 230-260.

As mentioned above, each of the groupings of apertures is associated with a chamber, which chamber and the features thereof further define one of the clamps 320-329. An exemplary clamp (for example, clamp 325) is illustrated in larger scale in FIG. 7 so that the cooperation of the structures of the chamber may be visualized (the structures of the corresponding channels have been omitted for ease of illustration). While the clamp illustrated in FIG. 7 has only two apertures in cross-section, this structure also is applicable to those clamps that have more than two apertures.

The clamp illustrated includes a chamber wall 340 that is formed as part of the frame 222, and extends from a frame wall 342. The chamber wall 240 encloses a circular region as viewed in FIG. 5, and thus may also be described as a circumferential or peripheral wall. The side wall 226, which may be made of a flexible material, is attached to an edge 344 of the chamber wall 340, and with the chamber wall 340 and the frame wall 342 define an enclosed region or space 346. The apertures 292, 294 pass through the frame wall 342, and one of the apertures 294 has a rim or flange 350 disposed about its circumference or periphery. The distance of an edge 352 of the rim 350 from the frame wall 342 is not as great at the distance of the edge 344 from the frame wall 342.

As illustrated in dashed line in FIG. 7, a portion of the wall 226, also referred to as a deflectable surface, may be brought into contact with the edge 352 of the rim 350 to cover the aperture 294 so that fluid cannot flow between the aperture 294 and the volume or space 346. At the same time, the fluid flow between the aperture 292 and the space 346 may remain unobstructed because the deflectable surface does not cover the aperture 292. However, by closing the aperture 294, fluid flow may be interrupted along the fluid path defined by the channels 244, 250 associated with the apertures 294, 292, respectively. The wall 226 may be selectively deflected to abut the rim 350 through the use of an actuator 354 coupled to the controller 150, which actuator 354 may be defined in part by a shaft 356 that moves along an axis 358 (for example, where the shaft 356 is part of an electronic linear actuator). When the shaft 356 is advanced in the direction of the wall 342, the shaft 356 deflects the wall 226 to abut the edge 352 and close the aperture 294. When the shaft 356 is withdrawn away from the wall 342, the wall 226 moves away from the edge 352 and the aperture 294 is open and in fluid communication with the space 346.

Figure 8:
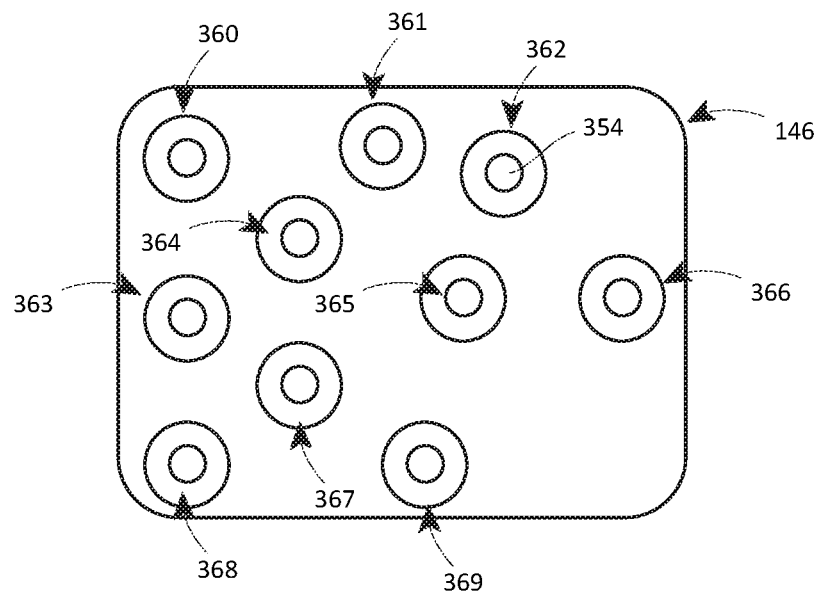
FIG. 8 is a plan view of an embodiment of a flow control interface that is associated with the flow control cassette, and which is configured to operate the selectable junctions, or clamps, of the flow control cassette.

As illustrated in FIG. 8, the cassette interface 146 may include a plurality of actuators 354, each within a space that is intended to be aligned with one of the clamps 320-329. The actuators 354 each may define one of a plurality of actuator stations 360-369 that corresponds to a respective one of the clamps 320-329. Each of the actuators stations 360-369 may be coupled to the controller 150, as illustrated in FIG. 3, and the controller 150 may control the movement of the actuators 354 in the direction of and away from the cassette 130 when the cassette 130 is disposed or mounted on the cassette interface 146. The controller 150 may operate the actuators 354 in conjunction with the desired process.

The cassette 130 may also include a number of air sensor chambers 330-334 disposed at points along the periphery of the frame 222. See FIG. 5. The cassette 130 is to be used with air sensors that are associated with each of the air chambers 330-334 such that it is not necessary that the emitter and detector be disposed on opposite sides of the frame 222. Instead, the emitter and detector can be disposed on the same side of the frame 222, providing so-called single-sided air sensor. This may be beneficial as there is no need to provide a door to close over the cassette 130, the door having either an emitter or a detector mounted thereon, as would be the case with a pass-through sensor where the emitter and detector must be disposed on opposite sides of the cassette 130.

The single-sided air sensors may be in the form of an ultrasonic sensor that emits controlled, timed pulses of ultrasonic energy into the chamber 330-334 and senses the response time of the "echo" of the emitted energy. The echo time is believed to change when the liquid enters the chamber. As an alternative, each of the chambers may have a window that permits an optical sensor to be used therewith, the window being translucent at least to light of a wavelength emitted by a light emitter associated with the sensor. A single-sided (reflectance-based) optical sensor may be used to determine other things than the presence of an air/fluid interface, such as cell concentrations in the fluid as well.

In addition to the cooperation between the cassette 130 and the cassette interface 146, the disposable fluid circuit 102 and the reusable hardware 104 cooperates in other ways as well.

Figure 9:
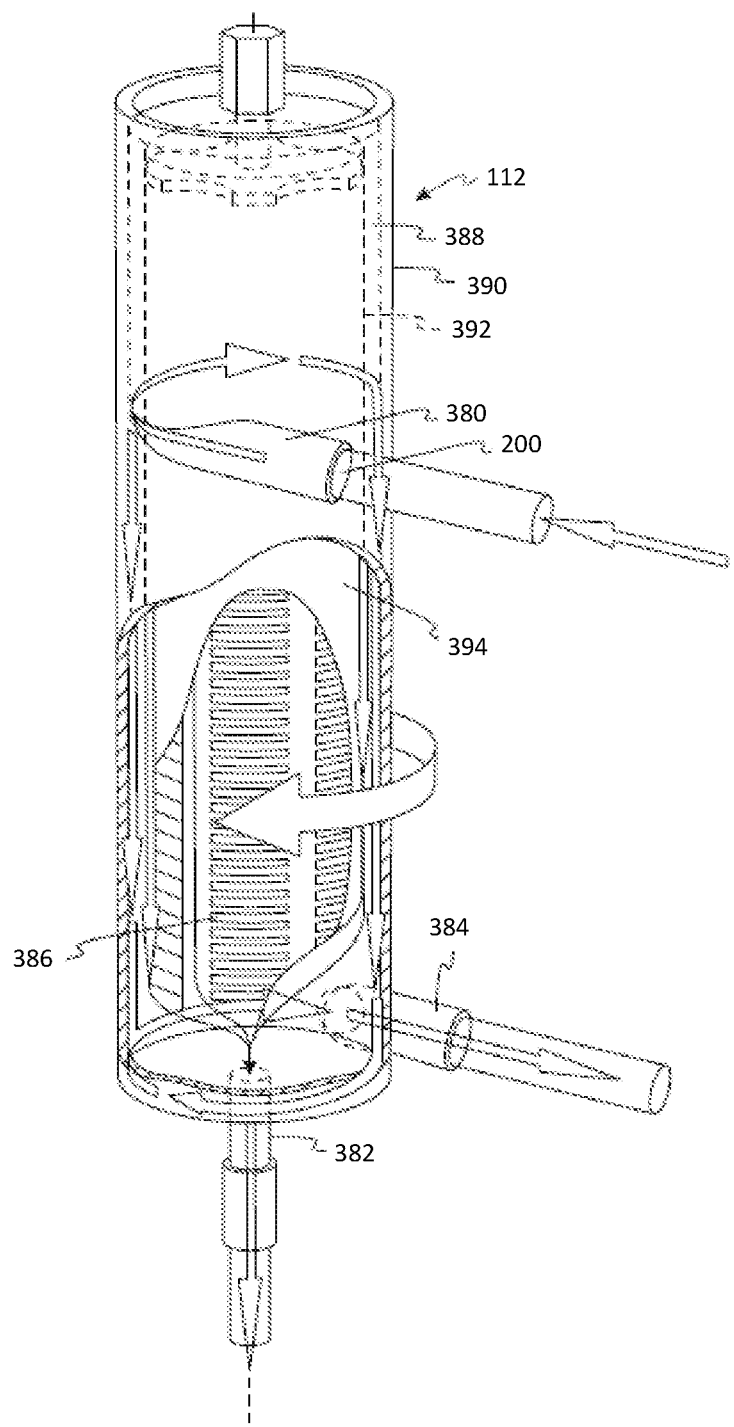
FIG. 9 is a perspective view of a separation/washing device using a spinning membrane.

FIG. 9 illustrates additional details of the spinning membrane separator 112, for example. Preferably, spinning membrane 112 is a spinning membrane separator of the type described in U.S. Pat. Nos. 5,194,145 and 5,053,121, U.S. Provisional Patent Application No. 61/451,903 and PCT Patent Application No. PCT/US2012/028522, which are incorporated herein by reference in their entirety. As discussed above, the spinning membrane separator 112 has one inlet 380 at least two outlet ports 382, 384. The outlet 382 of spinning membrane 112 receives the waste from the wash (i.e., a non-cellular component of the cellular suspension and wash medium from the spinning membrane separator) and is connected to line 204. The spinning membrane 112 preferably includes a second outlet 384 that is connected to line 206 and receives the desired biological cell/fluid product (e.g., washed cells).

Figure 10:
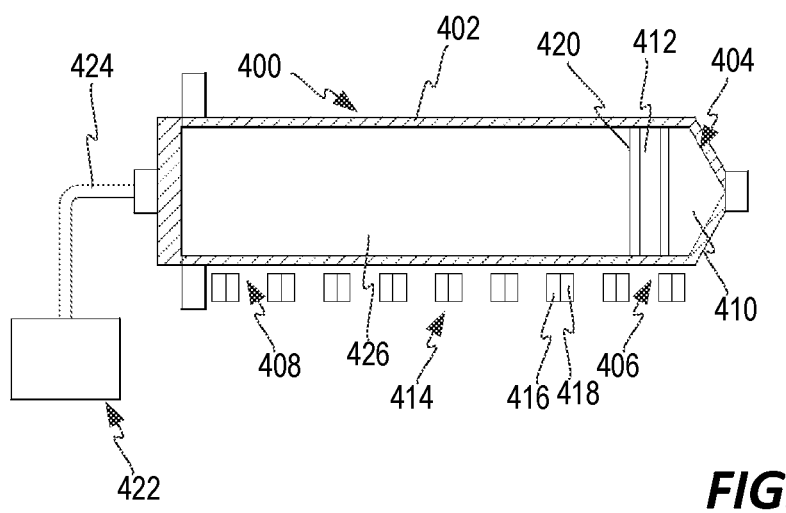
FIG. 10 is a cross-sectional view of an embodiment of a syringe/syringe pump as may be used as part of the system of FIG. 1, with a piston head assembly in a first position.
Figure 11:
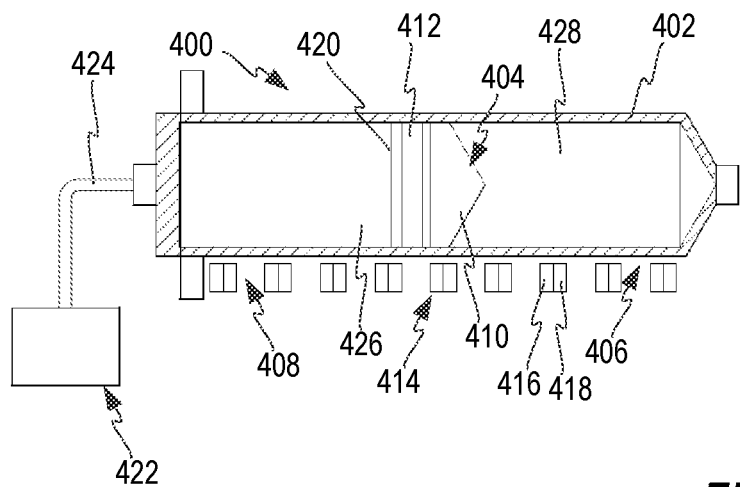
FIG. 11 is a cross-sectional view of the syringe/syringe pump of FIG. 10, with a piston head assembly in a second position.

FIGS. 10 and 11 illustrate an embodiment of a syringe pump that may be used with either the first or the second syringe 116, 118 and as either the first and/or second syringe pump 142, 144.

The syringe pump is configured to use a syringe 400 with a syringe barrel 402 (which may be made of cyclic olefin copolymer, or other materials such as may be inert, optically clear) and a piston or plunger head assembly 404. The piston head assembly 404 is moveable (translatable) between a first end 406 and a second end 408 of the barrel 402.

The piston head assembly 404 includes the piston 410 and an infrared reflector 412, which defines one part of a position detector 414. According to the illustrated embodiment, the position detector 414 also includes a plurality of transmitter/sensor pairs 416, 418. According to the illustrated embodiment, the transmitters (or emitters) 416 may be in the form of infrared light emitting diodes, and the sensors 418 may be in the form of infrared sensors. According to other embodiments, the transmitters and sensors may use visible or ultraviolet light, for example. The transmitter/sensor pairs 416, 418 are disposed along the length of the barrel 402 between the first end 406 and the second end 408. The reflector 412 may be in the form of a reflective strip that is disposed about the perimeter of a rigid disc 420 that is attached opposite the piston 410.

Figure 12:
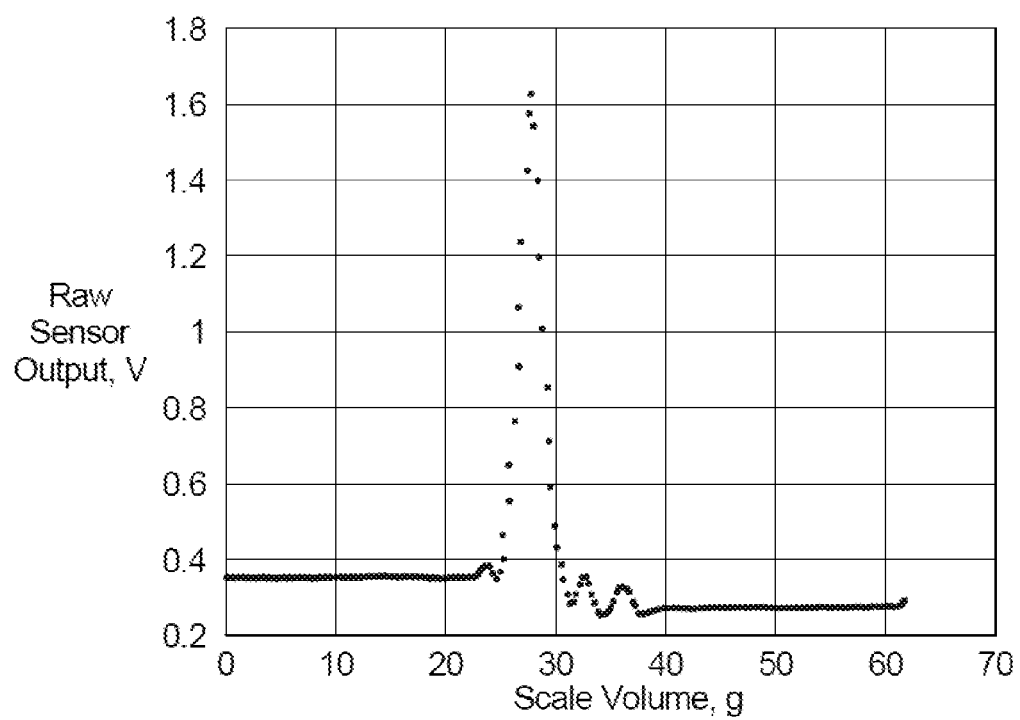
FIG. 12 is a chart of the signal response of one of the infrared detectors or sensors of the syringe/syringe pump of FIG. 10.

In operation, the position detector 414 (which could be coupled to the controller 150, for example) would use the interaction between the transmitter/sensor pairs 416, 418 and the reflector 412 to determine the positon of the piston head assembly 404 along the barrel 402. In particular, light emitted from the transmitter 416 would be received by the sensor 418 (or would be received over a threshold amount) if the light contacts the reflector 412. Otherwise, the light would not be received by the sensor 418 (or would not be received below the threshold amount). Depending on the amount of light received by the sensor 418, a signal generated by the sensor 418 would vary. See, e.g., FIG. 12, wherein the signal of the sensor 418 varies as the piston head assembly 404 is drawn to the second end 408, with the sensor signal representative of first air, then piston o-ring, reflector 412 (corresponding to the peak in sensor output), piston, and finally fluid opposite the sensor 418. Depending on the signals received from the individual transmitter/sensor pairs 416, 418, the controller 150 may determine the position of the piston head assembly 404 along the barrel 402 between the first and second ends 406, 408.

A vacuum/pressure source (e.g., a diaphragm pump) is attached via line (e.g., tubing) 424 to the end 408 of the barrel 402. The end 408 is otherwise closed, forming a first variable volume space 426 between the closed end 408 of the barrel 402 and the piston head assembly 404. Filtered air may be pumped into and out of the space 426 to cause the piston head assembly 404 to move between the first and second ends 406, 408 of the barrel 402. The movement of the piston head assembly 404 causes a second variable volume space 428 to open between the piston head assembly 404 and the first end 406 to receive fluid (e.g., a cell product) into the barrel 402. Compare FIGS. 10 and 11. Fluid may be drawn into (or may enter into) and pushed or delivered from the space 428 according to the movement of the piston head assembly 404.

In operation, the piston head assembly 404 starts at a first position, such as is illustrated in FIG. 10. The controller 150 causes the vacuum/pressure source to operate, and draw vacuum behind the piston head assembly 404 (i.e., in space 426). As a consequence, the piston head assembly 404 moves in the direction of the end 408 (i.e., from the end 406 to the end 408) and draws fluid into the space 428 (see FIG. 11). The controller 150 may subsequently operate the vacuum/pressure source to pump pressurized air into the space 426. This causes the piston head assembly 404 to move in the direction of the end 406 (i.e., from the end 408 to the end 406) and push fluid from the space 428.

It will be recognized that the pneumatic control of filtered air in and out of the space 426 provides certain advantages over the use of a syringe with a plunger arm where one end of the barrel remains open to the surrounding environment. By leaving the barrel end open, materials could collect on an inner surface of the barrel wall, such that movement of the piston head between the ends could permit the materials on the inner surface to interact with the fluid on the other (i.e., wet-side) of the piston head. The use of filtered air in the space 426 to move the piston 410 reduces or eliminates this potential source of contaminants. Further, the position detector 414 permits very precise control of the operation of the syringe pump 400. Other embodiments may use a mechanical or electro-mechanical mechanism to move the piston head 410, however.

Having discussed the structure of the illustrated embodiment of the fluid circuit 102 and the corresponding equipment of the reusable hardware 104, the operation of the system 100 is now discussed with reference to FIG. 13. As much of the operation of the system 100 involves control of the fluid flow between the containers 110, 114, 120, 122, 124, 126, 128, the syringes 116, 118, and the spinning membrane 112 through the cassette 130, reference is also made to FIGS. 1,2 and 6.

A method 450 of operating the system 100 may begin with one or more pre-processing actions at blocks 452, 454, 456. While each block 452, 454, 456 describes a different general type of activity, the actions at blocks 452, 454, 456 may include a plurality of individual actions. For example, priming the circuit 102 at block 456 may include individual actions of priming different portions of the circuit 102, but for ease of illustration, the actions have been grouped together at block 456.

Starting then with block 452, the circuit 102 is installed on the hardware 104. The controller 150 may determine when this is complete by checking one or more sensors, or the controller 150 may wait for an input to be received from the user via an input device, such as a touch screen. Once the controller 150 has determined that the circuit 102 is installed, the method passes to block 454.

At block 454, the controller 150 may perform numerous tests on the circuit 102 before any fluid is added to the circuit 102. Certain tests, or checks, are performed on the syringe pumps 142, 144, other checks are performed on the clamps 320-329. Because no fluid has been introduced to the circuit 102, these checks may be referred to as dry checks. After the checks have been performed, the containers 122, 124, 126, 128 containing the solutions for the process to be performed using the system may be connected to the circuit 102, and in particular to the lines 166, 168, 176, 180.

The first set of actions may be performed on the syringes 116, 118 and the syringe pumps 142, 144. Initially, the pistons (e.g., 410) of the syringes 116, 118 are drawn to the second end of the syringe (e.g., end 408, which end may be referred to as the upper end with the syringes 116, 118 in the orientation of FIG. 1) and then to the first end of the syringe (e.g., end 406, which end may be referred to as the lower end with the syringes 116, 118 in the orientation of FIG. 1), which is done to permit sensor normalization to be conducted (typically either when the piston is at the second end or the first end). During these actions, all of the clamps 320-329 are left open. A circuit (or kit) integrity check is then performed by moving the pistons of the syringes 116,118 to the second end of the syringe with only clamps 320, 321 closed. If the piston of either syringe 116, 118 is able to move toward the second end, then this suggests a leak in the circuit 102 or that the clamp 321 is unable to maintain a vacuum.

After the first set of actions, further checks are performed on the clamps 320-329. For example, clamps 322 and 325 may be closed, while the remainder of the clamps are open, and the piston of syringe 116 is moved toward the second end. Clamp 320 is then closed after a period of time, which should cause the piston in syringe 116 to stop moving and a negative pressure to build in the syringe 116. A similar process can be conducted for other clamps. For example, clamps 321, 322, 326 can be tested with all clamps except clamps 321, 322, and 326 closed, and then each of clamp 321, 322, 326 closed some time after the piston of syringe 116 is moved toward the second end. For clamp 329, all clamps 320-328 are closed and the piston of syringe 118 is moved toward the second end. The clamp 320 may also be checked again using the second syringe pump 144 and the second syringe 118, with the process being generally the same except that clamps 320, 322, 325, 326 are left open, and the piston of syringe 118 is advanced towards its second end.

Once the checks have been performed, the method 450 continues with the containers 110, 122, 124 and potentially container 126 being attached at the end of the actions of block 454 or the beginning of block 456. With the containers 110, 122, 124 attached, the circuit 102 may be primed at block 456.

The priming of the circuit 102 may start with the priming of the fluid path to the second syringe pump 144. To do this, the controller 150 may open clamps 324, 326 (remainder closed) and cause the piston of the second syringe 118 to move toward the second end. This draws wash fluid from the container 122, 124 through the port 174 and the channels 248, 250, 252 into the inlet 380 of the spinning membrane 112. The fluid passes through the spinning membrane 112, through port 210 and channels 236, 254 into the port 196 and syringe 118.

The fluid in the syringe 118 may be used to prime the path between the syringe pump 144 and the vent port 212 by closing all clamps except 321. The piston of the syringe 118 is then moved toward the first end to force fluid from the syringe 118 into channels 236, 234.

The priming of the circuit 102 may continue with the priming of the fluid path to the first syringe pump 142. To do this, the controller 150 opens clamps 322, 324 (remainder closed) and causes the piston of the first syringe 116 to move toward the second end. This draws wash fluid from the container 122, 124 through the port 174 and the channels 248, 250, 252 into the inlet 380 of the spinning membrane 112. The fluid passes through the spinning membrane 112, through port 208 and channels 232, 240, 242 and into the port 192 and syringe 116.

The fluid drawn into the first syringe 116 may be used to prime the fluid path to the source container 110. The controller 150 opens clamps 325, 327 and causes the piston of the first syringe 116 to move toward the first end. This pushes wash fluid from the syringe 116 through the port 192 and through channels 232, 244, 250, 256 to port 182. The fluid is able to pass from channel 232 to channel 244 because of the multiple apertures in clamp 322 that remain open to the chamber associated with that clamp even when the clamp 322 is closed. The fluid is pushed from the port 182 along the line 180 and into source container 110. This priming step removes air from the line 180 such that the system 100 is ready to begin processing cells.

The method 450 continues at block 458 with the controller 150 operating the system 100 to perform a procedure according to a protocol on the fluid in the source container 110. As one example, the controller 150 may operate the system 100 to separate cells from the fluid in the container 110, rinse the container 110 and wash the cells, and then pass the washed cells to container 128 for additional processing. As was the case with the actions at blocks 252, 254, 256, the actions at block 258 may include numerous individual actions, at least some of which may be repeated according to the amount of fluid in the source container 110, for example.

Figure 13:
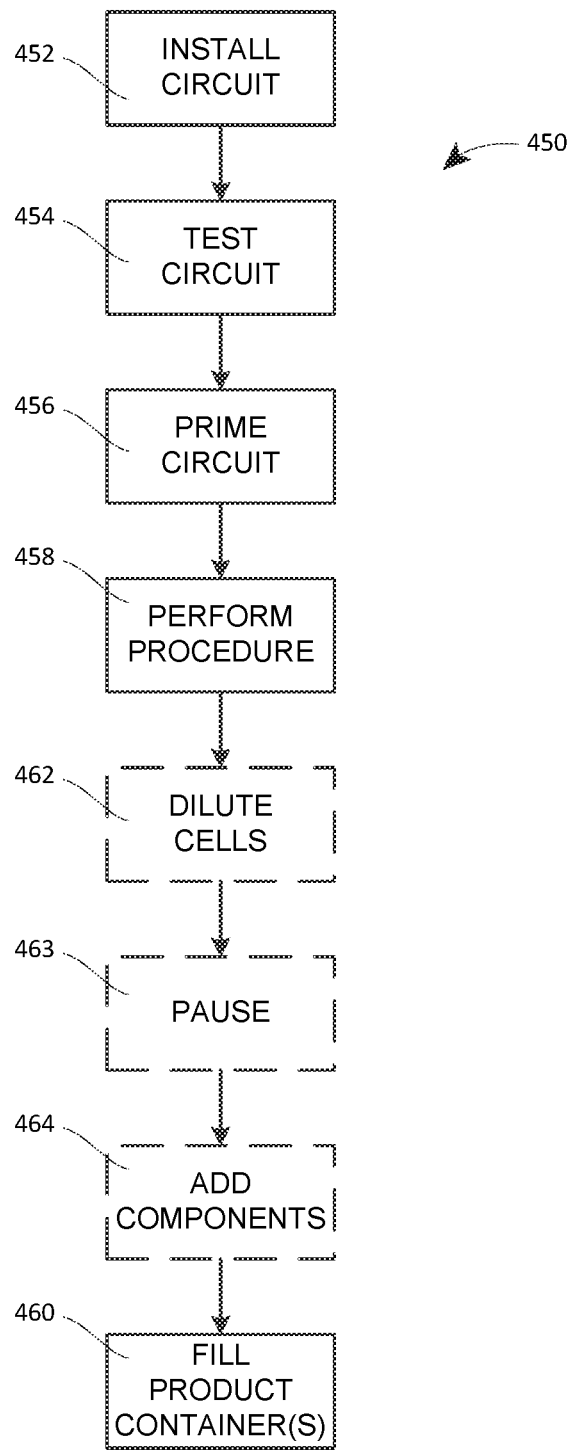
FIG. 13 is a flowchart illustrating an embodiment of a method of operating the system of FIG. 1.
Figure 14:
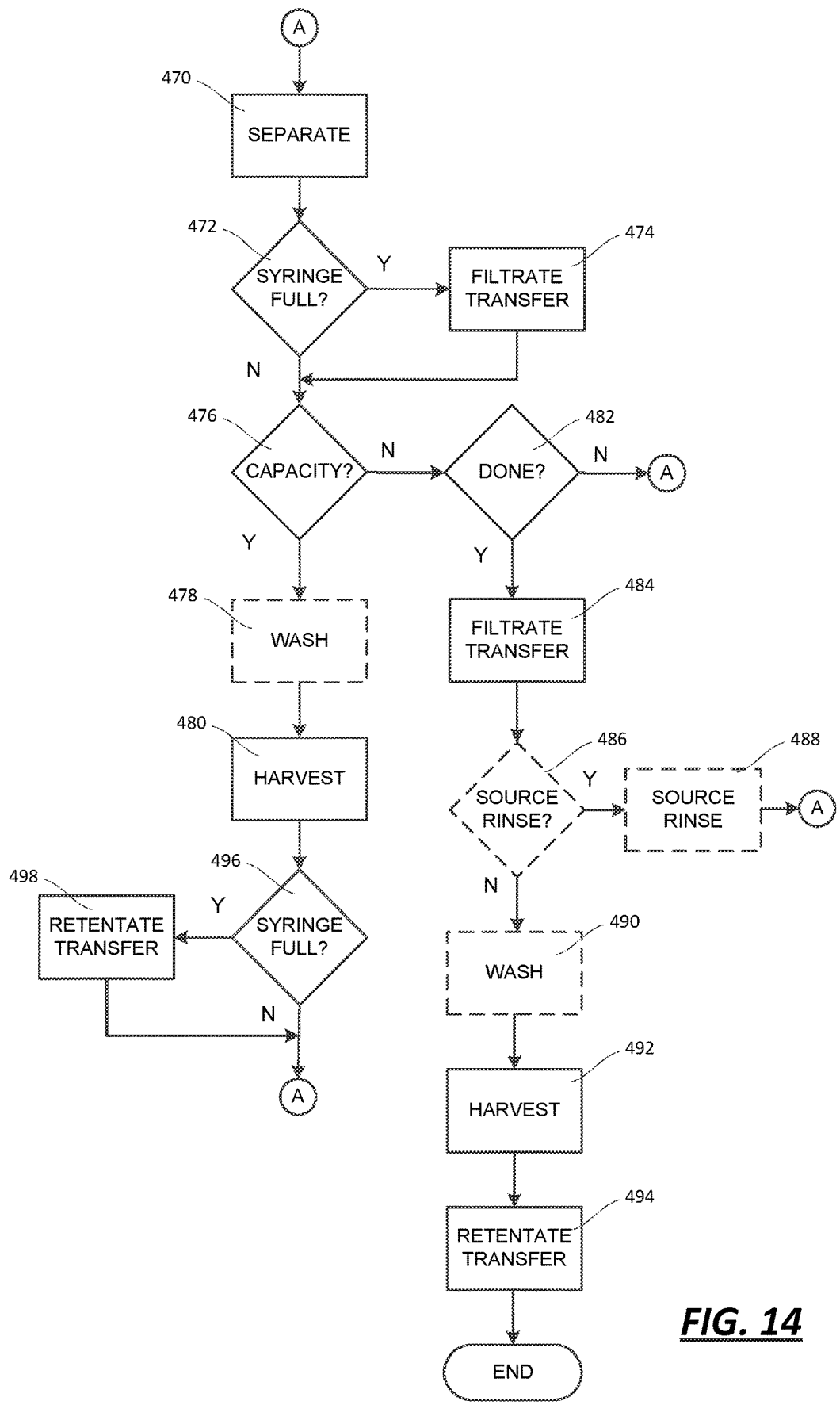
FIG. 14 is a flowchart illustrating an embodiment of a procedure that may be performed according to a protocol using the system 100.

In this regard, a further flowchart is provided in FIG. 14 to illustrate the actions of the block 258 in FIG. 13. In general terms, the separation of the cells from the fluid in the container 150 requires that the cells be transferred from the container 110 to the spinning membrane 112, the spinning membrane 112 be operated to separate the cells from the filtrate, the filtrate transferred first to the syringe 116 and then to the container 120, and the cells transferred first to the syringe 118 and to the container 128, at least according to the illustrated embodiment. Certain of the actions illustrated in FIG. 14 follow in a necessary order, for example, operating the syringe pump 142 occurs as a consequence of a determination that the syringe 116 is full. On the other hand, certain actions may be performed in any order; for example, the determination if the syringe 116 is full may follow the determination if the spinning membrane 112 is full, rather than the order illustrated. Some of the actions may be optional, and an attempt has been made to represent optional actions with the use of dashed line.

To perform the separation of the cells from the fluid in the container 110 at block 470, clamps 322, 327 may be opened (remainder closed) and the piston of syringe 116 is moved toward the second end. This draws fluid from the source container 110 into the port 182, channels 250, 252, 256 and into inlet 380 of the spinning membrane 112. Fluid is drawn from the spinning membrane 112 through ports 208 and channels 232, 240, 242 into the port 192 and the syringe 116. While the fluid and cells are flowing into the spinning membrane 112, a rotor 386 of the spinning membrane 112 rotates at a separation rate defined by the protocol, and fluid is drawn from the spinning membrane 112 while the target cells accumulate in an annulus 388 of the spinning membrane 112 between an outer housing 390 of the spinning membrane 112 and an outer surface 292 of a membrane 394. See FIG. 9. The cells accumulate in the annulus 388 because the clamp 326 is closed.

Depending on the amount of fluid present in the container 110, it may be necessary to empty the syringe 116 from time to time into the filtrate container 120. This may be done when the syringe 110 is full or reaches a certain threshold volume, as determined at block 472. This may also be done when the system needs to reset the position the filtrate syringe piston at the first end (e.g., end 406), for example. At block 474, the controller 150 opens only clamp 320 while causing the piston of the syringe 116 to move in the direction of the first end, causing fluid to flow along the fluid path defined by channels 230, 232, port 164, and line 162 into the container 120.

Depending on the accumulation of the cells in the annulus 388 of the spinning membrane 112, it may be desirable to wash the cells in the spinning membrane 112 and move the cells to the syringe 118 (which may be referred to as harvesting the cells). See blocks 476, 478, 480. If the capacity of the spinning membrane 112 is not reached before the source container 110 is emptied (as determined at block 482, for example), then the cell wash may be conducted after other actions have occurred, namely the rinsing of the source container 110. See blocks 484, 486, 488, 490, 492. It is possible for the cell wash and harvest to be performed multiple times (e.g., once when the capacity of the spinning membrane 112 is reached at blocks 480, 482 and once after the source container 110 is emptied at block 490, 492). According to certain embodiments, the cell wash at blocks 478, 490 may not be performed, and the source rinse at blocks 486, 488 may also be optional.

To perform a cell wash (block 478, 490), the controller 150 opens the clamps 322, 324 (remainder closed) and controls the piston of the syringe 116 to draw fluid from the containers 122, 124 through the port 174 and channels 248, 250, 252, through the spinning membrane 112, port 208, and channels 232, 240, 242 and into the syringe 116. This causes the fluid originally surrounding the cells (which may be referred to as original supernatant) to be replaced with new solution (i.e., the wash media). To harvest the cells (block 480, 492), the controller 150 leaves clamp 324 open, closes clamp 322, and opens clamp 326. The piston of syringe 118 is caused to move toward the second end to draw fluid from the containers 122, 124 through the port 174 and channels 248, 250, 252, through the spinning membrane 112, port 210, and channels 236, 254 and into the syringe 118.

When the source container 110 is emptied (block 482), the controller 150 may operate the system 100 to rinse the source container 110 (block 486), after which a cell wash and harvest is performed. To perform the rinse (block 488), the controller 150 first empties the syringe 116. Then, the controller 150 closes the clamp 320, and opens clamps 324, 325 (remainder closed) and moves the piston of the syringe 116 to draw fluid from the containers 122, 124 through port 174 and channels 232, 244, 248, 250 and into port 192 and syringe 116. Once a volume of the wash media has been drawn (or loaded) into the syringe 116, the syringe 116 is ready to deliver the rinse to the source container 110. To do so, the controller 150 leaves clamp 325 open, closes clamp 324, and opens clamp 327. The controller 150 then causes the piston of syringe 116 to push fluid through channels 232, 244, 250, 256 and port 182 into the source container 110.

With the wash media transferred to the source container 110, the controller 150 can conduct a wash and harvest (blocks 490, 492).

At this point (block 494) or earlier if the syringe 118 is determined to be full (see blocks 494, 496), the contents of the syringe 118 may be transferred to the product container(s) 114. See also, block 460 of FIG. 13. Alternatively, according to the illustrated embodiment, the contents of the syringe 118 may be transferred to the container 128 at blocks 494, 498, where the concentration of the cells may be modified and other components may be added at blocks 462, 464, after which the product containers are filled at block 460. According to the illustrated embodiment, the component added may be a cryopreservation agent (or CPA).

To begin, the contents of the syringe 118 are transferred to the container 128. The controller 150 opens only clamp 329, and causes the piston of the syringe 118 to move in the direction of the first end. This pushes the contents of the syringe 118 through channels 236, 260 and port 186 into line 184 and container 128. The controller 150 then closes the clamp 329 and opens clamps 324, 326, and draws fluid into the syringe 118 through port 174 from containers 122, 124, into channels 248, 250, 252, the spinning membrane 112, and channels 236, 254, and to the port 196. The controller then closes clamps 324, 326, opens clamp 329, and causes the piston of syringe 118 to move in the opposite direction to push the contents (wash media) from the syringe 118 into container 128.

According to the illustrated embodiment, the controller 150 may pause the method 450 at block 463. In fact, the controller 150 may pause the method 450 twice: once to permit a sample to be drawn from the container 128, and a second time to permit the container 126 to be connected to the circuit 102 if the container 126 was not attached previously. Once the desired activities have been conducted, the method continues with the addition of the CPA.

As part of the addition of the CPA to the container 128, the controller 150 may first open only clamp 323 and cause the syringe 118 to draw CPA solution from the container 126 via line 176 and port 178 and through channels 236, 238, 246 into the syringe 118. At this point, the clamp 323 is closed, and clamp 321 may be opened to permit the syringe 118 to push any excess air from the syringe 118 and out the vent port 212 and filter 214 via channels 234, 236. Preferably, enough air is left in the syringe 118 to have an air chase from the second syringe pump 144 to the container 128. The controller 150 then closes clamp 321, opens clamp 323 and draws the desired volume of CPA solution from container 128 via line 176 and port 178 and through channels 236, 238, 246 into the syringe 118. The controller 150 closes clamp 323, opens clamp 329 and moves the piston of syringe 118 to push the CPA solution from the syringe 118 into the container 126.

As illustrated, the embodiment of the system 100 includes a table 500 (see FIGS. 1 and 3) on which the container 128 is disposed to oscillate therewith. The table 500 may be mounted on a motor-drive shaft 502 that permits the table 500 to oscillate about an axis 504. The controller 150 may control the table 500 (via the motor) to cause the table 500 to oscillate to agitate the contents of the container 128, encouraging mixing of the contents. This agitation may be performed, for example, while the CPA solution is being added to the container 128. The agitation may be continued for an additional time after the CPA solution has been added to encourage adequate mixing. The table 500 may also include a cooling or heating element that permits the material in the container 128 to be maintained at a particular temperature.

According to certain embodiments, the container 128 may be detached from the circuit 102. However, according to the illustrated embodiment, the contents of the container 128 are instead filled into one or more product containers 114 that are attached to the circuit 102. The system 100 may include a scale 506 (see FIGS. 1 and 3) for weighing the contents of the container(s) 114, although the sensitive nature of the volume control on the syringe pump 144 makes the use of the scale 506 more in the nature of a secondary check.

To begin the fill activity, the controller 160 opens the clamp 329 and causes the syringe pump 144 to draw fluid from the container 128 via line 184 and port 186 into channels 236, 260. to prime the fluid path between the container 126 and the pump 144. The controller 150 then closes the clamp 329 and opens clamp 321 to vent excess air from the syringe 118 via channels 234, 236. Preferably, an air chase volume remains in the syringe 118 if the final dose volume and air chase volume can be delivered in one syringe stroke. The air chase volume should be sufficient to fully move the final dose volume from the syringe 118 to the final container 114

The controller 150 then closes clamp 321 and opens clamp 329 and causes the syringe pump 144 to draw fluid from the container 128 via line 184 and port 186 into channels 236, 260 to fill the syringe 118 with the desired volume of product. The controller 150 then closes clamp 329, opens clamp 328, and causes the syringe pump 144 to push fluid from the syringe 118 to one of the containers 114. The controller 150 may close the clamp 328 and open the clamp 321 to permit air to be drawn into the syringe 118, which air is then pushed from the syringe 118 with the clamp 321 closed and the clamp 328 open to provide an air chase volume to force the product solution into the container 114.

The system 100 may include other equipment as part of the hardware 104, in addition to the equipment already discussed, as illustrated in FIGS. 1 and 3. For example, the system 100 may include a display 508 with touch screen 510 to permit information to be entered into the system, including information regard the protocol of the procedure to be carried out by the system 100. The display 508 may be an electronic display, for example, with the touch screen 510 mounted thereon. Other input devices may be included, such as a pointer (e.g., mouse) and keyboard or keypad. As illustrated in FIGS. 1 and 3, an input device in the form of a barcode reader 512 may be attached to the system 100 to permit information to be inputted into the system 100 (and the controller 150) by scanning or reading a barcode, such as may be applied to the fluid circuit 102 or one or more of the containers 110, 114, 120, 122, 124, 126, 128. Other output devices also may be included, such as one or more lights (e.g., light emitting diodes or bulbs) 514, which may be used to signal alerts, events or machine states to the operator.

The system 100 may also be used with one or more ancillary or secondary devices or peripherals, which peripherals may include valves, pumps, etc. to be used to control the filling of the product containers, for example. The system 100 (and in particular, the controller 150) may be in communication with the peripheral(s), and data may be transmitted back and forth between the system 100 and the peripheral(s) or may be shared between the system 100 and the peripheral(s). In fact, the peripheral(s) may have its own controller (as illustrated, which controller may include a microprocessor, other circuits or circuitry and one or more memories, which may be one or more tangible non-transitory computer readable memories, with computer executable instructions by which the microprocessor is programmed and which when executed by the microprocessor may cause the microprocessor to carry out one or more actions being stored on the memory/memories) that is in communication with the controller 150. According to at least one embodiment, the ancillary or secondary device may be in the form of an external array of valves that can control the passage of fluid between the fluid circuit and the product containers, and the state of the valves may be controlled or triggered by the controller 150 via communication between the controller 150 and the controller associated with the array of valves Thus, an improved method and system for processing (e.g., concentrating or washing) small volumes of biological cells has been disclosed, in conjunction with an improved method and system for filling low-volume containers with the small volumes of processed. The description provided above, and the other aspects provided below, are intended for illustrative purposes, and are not intended to limit the scope of the disclosure to any particular method, system, apparatus or device described herein.

Other Aspects

Aspect 1. A fluid processing system comprising:
a disposable fluid circuit comprising:
  a spinning membrane separator having an inlet, a retentate outlet, and
a filtrate outlet;
  first and second syringes; and
  a flow control cassette comprising a housing containing a plurality of separate channels connected at a plurality of selectable junctions, each of the selectable junctions selectively connecting at least two of the plurality of channels, the channels and selectable junctions defining at least a first path between a source container, the spinning membrane inlet, the filtrate outlet and the first syringe, a second path between the first syringe and a filtrate container, and a third path between a wash media container, the spinning membrane inlet, the retentate outlet and the second syringe; and
reusable hardware configured to accept the disposable fluid circuit and comprising:
  a spinning membrane separator drive coupled to the spinning membrane separator;
  first and second syringe pumps, the first and second syringes coupled to the first and second syringe pumps respectively, the first syringe pump configured to move a piston within the first syringe and the second syringe pump configured to move a piston within the second syringe;
  a control cassette interface having at least one actuator for each of the selectable junctions; and
  at least one controller coupled to the spinning membrane separator drive, the first and second syringe pumps, and the control cassette interface, the controller configured to selectively operate the drive, the first and second syringe pumps, and the interface to provide a procedure according to a protocol.

Aspect 2. The system according to aspect 1, wherein the flow control housing comprises a frame and at least one side wall, the side wall attached to the frame with the channels defined therebetween, a negative pressure applied to the side wall at least during the procedure.

Aspect 3. The system according to aspect 1 or 2, wherein the flow control housing comprises a frame with opposed sides, and the frame comprises at least one air sensor chamber and an associated air sensor disposed on only one of the opposed sides of the frame.

Aspect 4. The system according to claim 3, wherein the air sensor is an ultrasonic sensor.

Aspect 5. The system according to claim 3, wherein the air sensor is an optical sensor.

Aspect 6. The system according to any one of aspects 1-5, wherein the controller is configured to cause the first syringe to draw fluid from the source container along the first path, to push fluid from the first syringe to the filtrate container along the second path, and to draw fluid from the spinning membrane separator to the second syringe along the third path.

Aspect 7. The system according to aspect 6, wherein the spinning membrane separator comprises a rotor, and the controller is configured to rotate the rotor at a separation rate defined by the protocol as the first syringe draws fluid from the source container along the first path.

Aspect 8. The system according to aspect 6 or 7, wherein:
  the channels and selectable junctions define at least a fourth path between the wash container, the inlet, the filtrate outlet, and the first syringe; and
  the controller is configured to draw wash media from the wash container to the first syringe along the fourth path, and then to draw fluid from the spinning membrane separator to the second syringe along the third path.

Aspect 9. The system according to any one of aspects 6-8, wherein:
  the channels and selectable junctions define at least another path between a secondary container and the second syringe; and
  the controller is configured to push fluid from the second syringe to the secondary container along the another path, to draw wash media into the second syringe along the third path, and push wash media from the second syringe to the secondary container along the another path.

Aspect 10. The system according to aspect 9, wherein:
  the channels and selectable junctions define at least a further path between the second syringe and a cryoprotective agent (CPA) container containing CPA solution; and
  the controller is configured to draw CPA solution from the CPA container along the further path, and to push CPA solution from the second syringe to the secondary container along the another path.

Aspect 11. The system according to aspect 9 or 10, wherein:
  the reusable hardware comprises an oscillating table, the secondary container disposed on the table to oscillate therewith; and
  the controller is configured to oscillate the table to mix the contents of the secondary container.

Aspect 12. The system according to any one of aspects 9-11, wherein:
  the channels and selectable junctions define at least an additional path between the second syringe and one or more product containers; and
  the controller is configured to draw fluid from the secondary container along the another path, and to push fluid from the second syringe to one of the one or more product containers along the additional path.

Aspect 13. The system according to aspect 12, wherein there is a plurality of product containers.

Aspect 14. The system according to any one of aspects 1-13, wherein:
the first syringe is attached at a first end to the fluid control cassette and the first syringe pump comprises a vacuum/pressure source attached to a second end of the first syringe, the vacuum/pressure source pumping filtered air into and out of the first syringe to move the piston in the first syringe; and
the second syringe is attached at a first end to the fluid control cassette and the second syringe pump comprises a vacuum/pressure source attached to a second end of the second syringe, the vacuum/pressure source pumping filtered air into and out of the second syringe to move the piston in the second syringe.

Aspect 15. The system according to aspect 14, further comprising a first position detector comprising an infrared reflector attached to the piston of the first syringe and a plurality of transmitter/sensor pairs, and a second position detector comprising an infrared reflector attached to the piston of the second syringe and a plurality of transmitter/sensor pairs.

Aspect 16. The system according to any one of aspects 1-15, wherein:
each of the selectable junctions comprises at least two apertures, a first aperture of the at least two apertures in fluid communication with a first one of the channels and a second aperture of the at least two apertures in fluid communication with a second one of the channels, and a deflectable surface that covers the first aperture but not the second aperture, and
the flow control cassette comprises a frame and at least one flexible side wall attached to one side of the frame, a portion of the flexible side wall defining the deflectable surface.

Aspect 17. The system according to aspect 16, wherein the at least one actuator for the selectable junction selectively deflects the deflectable surface to cover the first aperture.

The invention claimed is:
1. A fluid processing system comprising:
a disposable fluid circuit comprising:
a spinning membrane separator having an inlet, a retentate outlet, and a filtrate outlet;
first and second plunger less syringes with each syringe having a movable piston head assembly; and
a flow control cassette comprising a housing containing a plurality of separate channels connected at a plurality of selectable junctions, each of the selectable junctions selectively connecting at least two of the plurality of channels, the channels and selectable junctions defining at least a first path between a source container, the spinning membrane inlet, the filtrate outlet and the first syringe, a second path between the first syringe and a filtrate container, and a third path between a wash media container, the spinning membrane inlet, the retentate outlet and the second syringe; wherein each of the selectable junctions comprises at least two apertures, a first aperture of the at least two apertures in fluid communication with a first one of the channels and a second aperture of the at least two apertures in fluid communication with a second one of the channels, and a deflectable surface that covers the first aperture but not the second aperture, and the flow control cassette housing comprises a frame and at least one flexible side wall attached to one side of the frame, a portion of the flexible side wall defining the deflectable surface; and
reusable hardware configured to accept the disposable fluid circuit and comprising:
a spinning membrane separator drive coupled to the spinning membrane separator;
first and second syringe pumps, the first and second syringes coupled to the first and second syringe pumps respectively, the first syringe pump configured to move the piston head assembly within the first syringe and the second syringe pump configured to move the piston head assembly within the second syringe;
a control cassette interface having at least one actuator for each of the selectable junctions; and
at least one controller coupled to the spinning membrane separator drive, the first and second syringe pumps, and the control cassette interface, the controller configured to selectively operate the drive, the first and second syringe pumps, and the interface to provide a procedure according to a protocol.

2. The system according to claim 1, wherein channels are defined the at least one flexible side wall and the frame, and a negative pressure is applied to the side wall at least during the procedure.

3. The system according to claim 1, wherein the flow control cassette housing frame comprises opposed sides, and the frame comprises at least one air sensor chamber and an associated air sensor disposed on only one of the opposed sides of the frame.

4. The system according to claim 3, wherein the air sensor is an ultrasonic sensor.

5. The system according to claim 3, wherein the air sensor is an optical sensor.

6. The system according to claim 1, wherein the controller is configured to cause the first syringe to draw fluid from the source container along the first path, to push fluid from the first syringe to the filtrate container along the second path, and to draw fluid from the spinning membrane separator to the second syringe along the third path.

7. The system according to claim 6, wherein the spinning membrane separator comprises a rotor, and the controller is configured to rotate the rotor at a separation rate defined by the protocol as the first syringe draws fluid from the source container along the first path.

8. The system according to claim 6, wherein:
the channels and selectable junctions define at least a fourth path between the wash container, the inlet, the filtrate outlet, and the first syringe; and
the controller is configured to draw wash media from the wash container to the first syringe along the fourth path, and then to draw fluid from the spinning membrane separator to the second syringe along the third path.

9. The system according to claim 6, wherein:
the channels and selectable junctions define at least another path between a secondary container and the second syringe; and
the controller is configured to push fluid from the second syringe to the secondary container along the another path, to draw wash media into the second syringe along the third path, and push wash media from the second syringe to the secondary container along the another path.

10. The system according to claim 9, wherein:
the channels and selectable junctions define at least a further path between the second syringe and a cryoprotective agent (CPA) container containing CPA solution; and
the controller is configured to draw CPA solution from the CPA container along the further path, and to push CPA solution from the second syringe to the secondary container along the another path.

11. The system according to claim 9, wherein:
the reusable hardware comprises an oscillating table, the secondary container disposed on the table to oscillate therewith; and
the controller is configured to oscillate the table to mix the contents of the secondary container.

12. The system according to claim 9, wherein:
the channels and selectable junctions define at least an additional path between the second syringe and one or more product containers; and
the controller is configured to draw fluid from the secondary container along the another path, and to push fluid from the second syringe to one of the one or more product containers along the additional path.

13. The system according to claim 12, wherein there is a plurality of product containers.

14. The system according to claim 1, wherein:
the first syringe is attached at a first end to the fluid control cassette and the first syringe pump comprises a vacuum/pressure source attached to a second end of the first syringe, the vacuum/pressure source pumping filtered air into and out of the first syringe to move the piston head assembly in the first syringe; and
the second syringe is attached at a first end to the fluid control cassette and the second syringe pump comprises a vacuum/pressure source attached to a second end of the second syringe, the vacuum/pressure source pumping filtered air into and out of the second syringe to move the piston head assembly in the second syringe.

15. A fluid processing system comprising:
a disposable fluid circuit comprising:
 a spinning membrane separator having an inlet, a retentate outlet, and a filtrate outlet;
 first and second plungerless syringes with each syringe having a movable piston head assembly; and
 a flow control cassette comprising a housing containing a plurality of separate channels connected at a plurality of selectable junctions, each of the selectable junctions selectively connecting at least two of the plurality of channels, the channels and selectable junctions defining at least a first path between a source container, the spinning membrane inlet, the filtrate outlet and the first syringe, a second path between the first syringe and a filtrate container, and a third path between a wash media container, the spinning membrane inlet, the retentate outlet and the second syringe; and
reusable hardware configured to accept the disposable fluid circuit and comprising:
 a spinning membrane separator drive coupled to the spinning membrane separator;
 first and second syringe pumps, the first and second syringes coupled to the first and second syringe pumps respectively, the first syringe pump configured to move the piston head assembly within the first syringe and the second syringe pump configured to move the piston head assembly within the second syringe;
 a control cassette interface having at least one actuator for each of the selectable junctions; and
 at least one controller coupled to the spinning membrane separator drive, the first and second syringe pumps, and the control cassette interface, the controller configured to selectively operate the drive, the first and second syringe pumps, and the interface to provide a procedure according to a protocol;
 wherein the first syringe is attached at a first end to the fluid control cassette and the first syringe pump comprises a vacuum/pressure source attached to a second end of the first syringe, the vacuum/pressure source pumping filtered air into and out of the first syringe to move the piston head assembly in the first syringe;
 the second syringe is attached at a first end to the fluid control cassette and the second syringe pump comprises a vacuum/pressure source attached to a second end of the second syringe, the vacuum/pressure source pumping filtered air into and out of the second syringe to move the piston head assembly in the second syringe;
 a first position detector comprising an infrared reflector attached to the piston head assembly of the first syringe and a plurality of transmitter/sensor pairs, and a second position detector comprising an infrared reflector attached to the piston head assembly of the second syringe and a plurality of transmitter/sensor pairs.

16. The system according to claim 15, wherein:
each of the selectable junctions comprises at least two apertures, a first aperture of the at least two apertures in fluid communication with a first one of the channels and a second aperture of the at least two apertures in fluid communication with a second one of the channels, and a deflectable surface that covers the first aperture but not the second aperture, and
the flow control cassette comprises a frame and at least one flexible side wall attached to one side of the frame, a portion of the flexible side wall defining the deflectable surface.

17. The system according to claim 16, wherein the at least one actuator for the selectable junction selectively deflects the deflectable surface to cover the first aperture.

18. A fluid processing system comprising:
a disposable fluid circuit comprising:
 a spinning membrane separator having an inlet, a retentate outlet, and a filtrate outlet;
 first and second plungerless syringes with each syringe having a movable piston head assembly; and
 a flow control cassette comprising a housing containing a plurality of separate channels connected at a plurality of selectable junctions, each of the selectable junctions selectively connecting at least two of the plurality of channels, the channels and selectable junctions defining at least a first path between a source container, the spinning membrane inlet, the filtrate outlet and the first syringe, a second path between the first syringe and a filtrate container, and a third path between a wash media container, the spinning membrane inlet, the retentate outlet and the second syringe; and reusable hardware configured to accept the disposable fluid circuit and comprising:
a spinning membrane separator drive coupled to the spinning membrane separator;
first and second syringe pumps, the first and second syringes coupled to the first and second syringe pumps respectively, the first syringe pump configured to move the piston head assembly within the first syringe and the second syringe pump configured to move the piston head assembly within the second syringe;
a control cassette interface having at least one actuator for each of the selectable junctions; and
at least one controller coupled to the spinning membrane separator drive, the first and second syringe pumps, and the control cassette interface, the controller configured to selectively operate the drive, the first and second syringe pumps, and the interface to provide a procedure according to a protocol;
wherein the controller is configured to cause the first syringe to draw fluid from the source container along the first path, to push fluid from the first syringe to the filtrate container along the second path, and to draw fluid from the spinning membrane separator to the second syringe along the third path;
the channels and selectable junctions define at least another path between a secondary container and the second syringe;
the controller is configured to push fluid from the second syringe to the secondary container along the another path, to draw wash media into the second syringe along the third path, and push wash media from the second syringe to the secondary container along the another path;
the channels and selectable junctions define at least a further path between the second syringe and a cryoprotective agent (CPA) container containing CPA solution; and
the controller is configured to draw CPA solution from the CPA container along the further path, and to push CPA solution from the second syringe to the secondary container along the another path.

19. A fluid processing system comprising:
a disposable fluid circuit comprising:
a spinning membrane separator having an inlet, a retentate outlet, and a filtrate outlet;
first and second plungerless syringes with each syringe having a movable piston head assembly; and
a flow control cassette comprising a housing containing a plurality of separate channels connected at a plurality of selectable junctions, each of the selectable junctions selectively connecting at least two of the plurality of channels, the channels and selectable junctions defining at least a first path between a source container, the spinning membrane inlet, the filtrate outlet and the first syringe, a second path between the first syringe and a filtrate container, and a third path between a wash media container, the spinning membrane inlet, the retentate outlet and the second syringe; and
reusable hardware configured to accept the disposable fluid circuit and comprising:
a spinning membrane separator drive coupled to the spinning membrane separator;
first and second syringe pumps, the first and second syringes coupled to the first and second syringe pumps respectively, the first syringe pump configured to move the piston head assembly within the first syringe and the second syringe pump configured to move the piston head assembly within the second syringe;
a control cassette interface having at least one actuator for each of the selectable junctions; and
at least one controller coupled to the spinning membrane separator drive, the first and second syringe pumps, and the control cassette interface, the controller configured to selectively operate the drive, the first and second syringe pumps, and the interface to provide a procedure according to a protocol;
wherein the controller is configured to cause the first syringe to draw fluid from the source container along the first path, to push fluid from the first syringe to the filtrate container along the second path, and to draw fluid from the spinning membrane separator to the second syringe along the third path;
the channels and selectable junctions define at least another path between a secondary container and the second syringe;
the controller is configured to push fluid from the second syringe to the secondary container along the another path, to draw wash media into the second syringe along the third path, and push wash media from the second syringe to the secondary container along the another path;
the reusable hardware further comprises an oscillating table, the secondary container disposed on the table to oscillate therewith; and
the controller is configured to oscillate the table to mix the contents of the secondary container.

20. A fluid processing system comprising:
a disposable fluid circuit comprising:
a spinning membrane separator having an inlet, a retentate outlet, and a filtrate outlet;
first and second plungerless syringes with each syringe having a movable piston head assembly; and
a flow control cassette comprising a housing containing a plurality of separate channels connected at a plurality of selectable junctions, each of the selectable junctions selectively connecting at least two of the plurality of channels, the channels and selectable junctions defining at least a first path between a source container, the spinning membrane inlet, the filtrate outlet and the first syringe, a second path between the first syringe and a filtrate container, and a third path between a wash media container, the spinning membrane inlet, the retentate outlet and the second syringe; and
reusable hardware configured to accept the disposable fluid circuit and comprising:
a spinning membrane separator drive coupled to the spinning membrane separator;
first and second syringe pumps, the first and second syringes coupled to the first and second syringe pumps respectively, the first syringe pump configured to move the piston head assembly within the first syringe and the second syringe pump configured to move the piston head assembly within the second syringe;
a control cassette interface having at least one actuator for each of the selectable junctions; and
at least one controller coupled to the spinning membrane separator drive, the first and second syringe pumps, and the control cassette interface, the controller configured to selectively operate the drive, the first and second syringe pumps, and the interface to provide a procedure according to a protocol;

wherein the controller is configured to cause the first syringe to draw fluid from the source container along the first path, to push fluid from the first syringe to the filtrate container along the second path, and to draw fluid from the spinning membrane separator to the second syringe along the third path;

the channels and selectable junctions define at least another path between a secondary container and the second syringe;

the controller is configured to push fluid from the second syringe to the secondary container along the another path, to draw wash media into the second syringe along the third path, and push wash media from the second syringe to the secondary container along the another path;

the channels and selectable junctions define at least an additional path between the second syringe and one or more product containers; and the controller is configured to draw fluid from the secondary container along the another path, and to push fluid from the second syringe to one of the one or more product containers along the additional path.

* * * * *